(12) United States Patent
Kawamoto et al.

(10) Patent No.: US 11,193,480 B2
(45) Date of Patent: Dec. 7, 2021

(54) EXHALATION MEASUREMENT DEVICE, AND CONTROL METHOD

(71) Applicant: PHC HOLDINGS CORPORATION, Tokyo (JP)

(72) Inventors: Toru Kawamoto, Ehime (JP); Jun'ichi Hyohgo, Ehime (JP); Takeshi Ohsora, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 1264 days.

(21) Appl. No.: 14/898,746

(22) PCT Filed: Jun. 16, 2014

(86) PCT No.: PCT/JP2014/003209
§ 371 (c)(1),
(2) Date: Dec. 16, 2015

(87) PCT Pub. No.: WO2015/001735
PCT Pub. Date: Jan. 8, 2015

(65) Prior Publication Data
US 2016/0135714 A1 May 19, 2016

(30) Foreign Application Priority Data

Jul. 3, 2013 (JP) .............................. JP2013-139808

(51) Int. Cl.
*F04B 45/047* (2006.01)
*A61B 5/097* (2006.01)
(Continued)

(52) U.S. Cl.
CPC ............ *F04B 45/047* (2013.01); *A61B 5/087* (2013.01); *A61B 5/091* (2013.01); *A61B 5/097* (2013.01);
(Continued)

(58) Field of Classification Search
CPC ....... A61B 5/7267; A61B 5/097; A61B 5/093; A61B 5/091; A61B 5/0871; A61B 5/087;
(Continued)

(56) References Cited

U.S. PATENT DOCUMENTS

| 5,239,319 A | * | 8/1993 | Miyazaki | ............... A61M 5/172 |
| | | | | 310/316.01 |
| 5,664,560 A | * | 9/1997 | Merrick | ................ A61M 16/12 |
| | | | | 128/203.25 |

(Continued)

FOREIGN PATENT DOCUMENTS

| EP | 1311315 | 5/2003 |
| JP | S64-015476 A | 1/1989 |

(Continued)

OTHER PUBLICATIONS

European Search Report from the corresponding European Patent Application No. 14820208.8 dated Mar. 24, 2016.
(Continued)

*Primary Examiner* — Matthew Kremer
*Assistant Examiner* — Avery M Foley
(74) *Attorney, Agent, or Firm* — McDermott Will and Emery LLP

(57) ABSTRACT

The exhalation measurement device of certain implementations comprise a chamber, a measurement component, a piezoelectric pump, a first learning controller, and a second learning controller. The chamber may temporarily hold exhalation. The measurement component may measure a specific component in the exhalation. The piezoelectric pump may supply the measurement component with the exhalation held in the chamber. The first learning controller may perform operational setting on the piezoelectric pump before the piezoelectric pump supplies the exhalation in the chamber to the measurement component. The second learn- (Continued)

ing controller may perform operational setting on the piezoelectric pump after the piezoelectric pump has started supplying the exhalation in the chamber to the measurement component, but before the measurement component performs its measurement.

13 Claims, 11 Drawing Sheets

(51) Int. Cl.
  *G01N 33/497* (2006.01)
  *A61B 5/091* (2006.01)
  *A61B 5/087* (2006.01)
  *A61B 5/00* (2006.01)

(52) U.S. Cl.
  CPC ......... *A61B 5/7267* (2013.01); *G01N 33/497* (2013.01); *A61B 2560/02* (2013.01)

(58) Field of Classification Search
  CPC . A61B 2560/02; G01N 33/497; F04B 43/095; F04B 43/046; F04B 17/003; F04B 45/053; F04B 45/047
  See application file for complete search history.

(56) References Cited

U.S. PATENT DOCUMENTS

| | | | |
|---|---|---|---|
| 5,795,787 A | 8/1998 | Silkoff et al. | |
| 6,010,459 A | 1/2000 | Silkoff et al. | |
| 6,349,724 B1* | 2/2002 | Burton | A61M 16/0057 128/204.18 |
| 2007/0084766 A1 | 4/2007 | Ishii et al. | |
| 2009/0206699 A1* | 8/2009 | Osano | F04B 43/046 310/317 |
| 2010/0031730 A1 | 2/2010 | Van Uitert et al. | |
| 2010/0288027 A1 | 11/2010 | Ishii et al. | |
| 2014/0275857 A1* | 9/2014 | Toth | A61B 5/087 600/301 |
| 2014/0305436 A1* | 10/2014 | Nitta | A61M 15/0085 128/204.25 |

FOREIGN PATENT DOCUMENTS

| | | |
|---|---|---|
| JP | H01-167475 A | 7/1989 |
| JP | H06-147104 A | 5/1994 |
| JP | H10-048206 A | 2/1998 |
| JP | 2000-506601 A | 5/2000 |
| JP | 2002-350340 A | 12/2002 |
| JP | 2007-113439 A | 5/2007 |
| JP | 2010-509586 A | 3/2010 |
| WO | 1997/038307 A1 | 10/1997 |
| WO | 02/02169 A1 | 1/2002 |

OTHER PUBLICATIONS

Search Report from the corresponding International Patent Application No. PCT/JP2014/003209 dated Sep. 16, 2014.

* cited by examiner

EXHALATION MEASUREMENT DEVICE, AND CONTROL METHOD

PRIORITY

This is a National Stage Application under 35 U.S.C. § 365 of International Application PCT/JP2014/003209, with an international filing date of Jun. 16, 2014, which claims priority to Japanese Patent Application No. 2013-139808 filed on Jul. 3, 2013. The entire disclosures of International Application PCT/JP2014/003209 and Japanese Patent Application No. 2013-139808 are hereby incorporated herein by reference.

TECHNICAL FIELD

Certain implementations relate to an exhalation measurement device used in checking pulmonary function, diagnosing asthma, and so forth, and to a method for controlling this device.

BACKGROUND

A conventional exhalation measurement device of this type comprised a chamber that temporarily holds exhalation, an electromagnetic pump that supplies the exhalation held in this chamber to a measurement component, and a controller that controls the operation of this electromagnetic pump.

Specifically, when an attempt was made to measure ammonia or the like contained in the exhalation by having the user blow directly into the measurement component, there was variance in the state of the exhalation blown into the measurement component, so the exhalation was first held in the chamber, and then the exhalation in this chamber was supplied to the measurement component by the electromagnetic pump.

SUMMARY

A problem encountered with the above prior art was that sensing accuracy was low sometimes. Specifically, a single stroke is long in an electromagnetic pump, so there is a larger pulsation in the exhalation flow supplied by the electromagnetic pump to the measurement component, and as a result there is more variance in the sensed value of the measurement component, and this lowers sensing accuracy.

In light of the problems encountered with conventional exhalation measurement devices, it is an object of certain implementations to provide an exhalation measurement device with higher sensing accuracy, as well as a method for controlling this device.

To achieve the stated object, the exhalation measurement device of certain implementations comprise a chamber, a measurement component, a piezoelectric pump, a first learning controller, a second learning controller, and a measurement controller. The chamber temporarily holds exhalation. The measurement component measures a specific component in the exhalation. The piezoelectric pump supplies the measurement component with the exhalation held in the chamber. The first learning controller performs operational setting on the piezoelectric pump before the piezoelectric pump supplies the exhalation in the chamber to the measurement component. The second learning controller performs operational setting on the piezoelectric pump after the piezoelectric pump has started supplying the exhalation in the chamber to the measurement component, but before the measurement component performs its measurement.

Specifically, certain implementations are configured such that the exhalation held in the chamber is supplied to the measurement component by the piezoelectric pump, and since a piezoelectric pump has a short stroke, there is less pulsation of the exhalation supplied by the piezoelectric pump to the measurement component, and as a result there is less variance in the sensed value of the measurement component, which allows the sensing accuracy to be improved.

Also, certain implementations are configured such that operational setting is performed on the piezoelectric pump before the piezoelectric pump supplies the exhalation in the chamber to the measurement component, and operational setting is performed on the piezoelectric pump after the piezoelectric pump has started supplying the exhalation in the chamber to the measurement component, after which the measurement component performs its measurement, which again improves sensing accuracy.

Specifically, with a piezoelectric pump, the optimal settings (such as drive frequency) vary with the usage environment (such as temperature), so with certain implementations, operational setting is performed on the piezoelectric pump before the exhalation in the chamber is supplied to the measurement component, and after the piezoelectric pump has started supplying the exhalation in the chamber to the measurement component.

Consequently, the piezoelectric pump is driven in an optimal state, and as a result the state of the exhalation supplied to the measurement component is stable, which improves the sensing accuracy.

Certain implementations provide an exhalation measurement device with improved sensing accuracy, as well as a method for controlling this device.

BRIEF DESCRIPTION OF THE DRAWINGS

FIG. 1 is an oblique view of an exhalation measurement device in;

DETAILED DESCRIPTION

Certain implementations of an exhalation measurement device will now be described through reference to the drawings.

Overview of Exhalation Measurement Device

Figure 1:
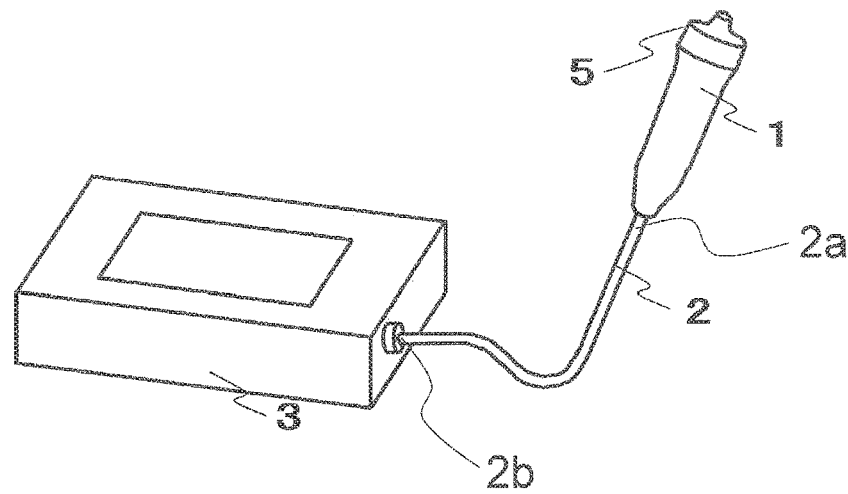

FIG. 1 shows an example of an exhalation measurement device for measuring the nitrogen monoxide contained in exhalation, which is correlated to a diagnosis of asthma.

As shown in FIG. 1, the exhalation measurement device in this implementation comprises a handle component 1 and a measurement device main body 3 that is connected to the handle component 1 by a tube 2.

The handle component 1 is configured to allow the user to blow exhalation into it. The user holds the handle component 1 and blows exhalation into it. One end 2a of the tube 2 is connected to this handle component 1, and the other end 2b of the tube 2 is connected to the measurement device main body 3, which is used to measure the exhalation that is blown in. That is, the handle component 1 is connected to the measurement device main body 3 via the tube 2.

Handle Component 1

Figure 2:
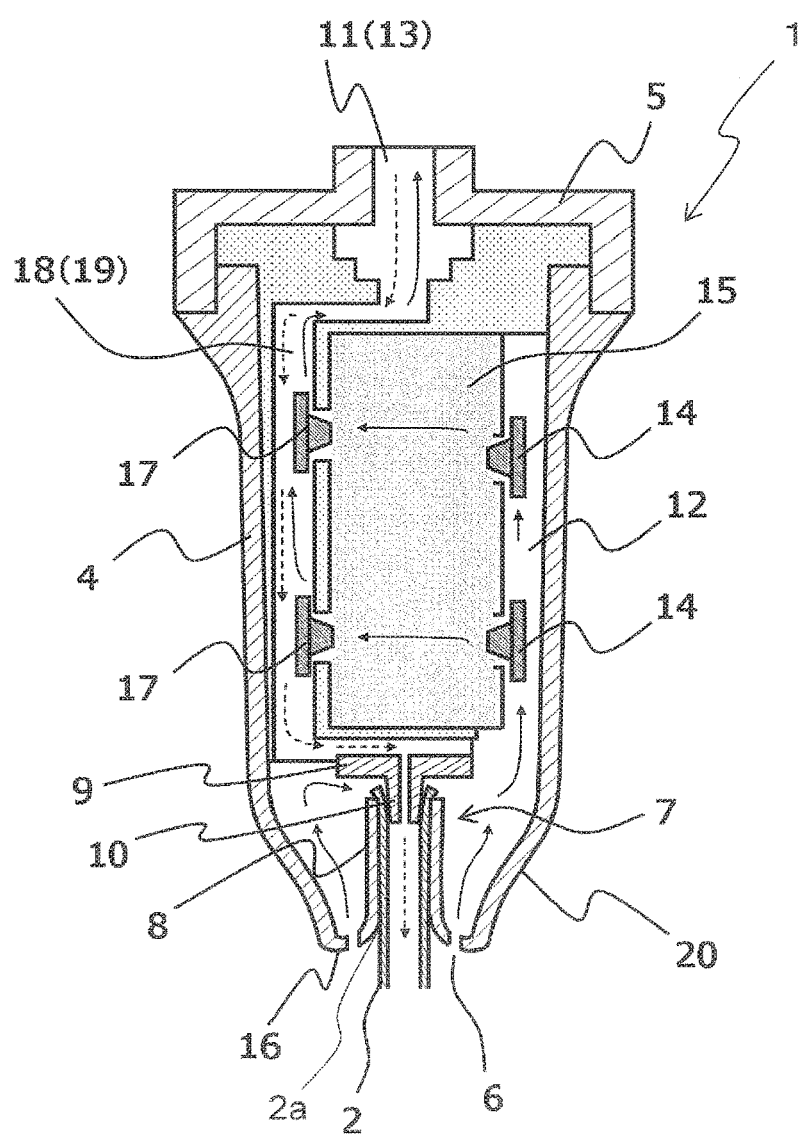
FIG. 2 is a cross section of a handle component of an exhalation measurement device.

FIG. 2 is a cross section of the handle component 1. As shown in FIG. 2, the handle component 1 is provided with a handle component main body 4, a mouthpiece 5 that is mounted above the handle component main body 4, inhalation holes 6 provided below the handle component main body 4, and a connector 7 that is connected to the end 2a of the tube 2.

This connector 7 is made up of a cylindrical part 8 of the handle component main body 4, and a connecting member 9 provided on the inside of the cylindrical part 8. A plurality of the inhalation holes 6 are formed in a ring shape around the cylindrical part 8.

The connecting member 9 has a small diameter part 10 whose diameter is smaller than that of the inner periphery of the cylindrical part 8.

The tube 2 is disposed between the outer peripheral face of the small diameter part 10 and the inner peripheral face of the cylindrical part 8. The tube 2 is fixed to the handle component main body 4 by squeezing the tube 2 between the small diameter part 10 and the cylindrical part 8.

The handle component main body 4 is further provided with a first inhalation channel 12 and a second inhalation channel 18 that connect the inhalation holes 6 with an inhalation inflow component 11 of the mouthpiece 5, and a discharge channel 19 that connects an exhalation discharge component 13 of the mouthpiece 5 with the end 2a of the tube 2. A filter 15 that removes from the air the component being measured by the exhalation measurement device of this implementation (nitrogen monoxide in this implementation) is provided between the first inhalation channel 12 and the second inhalation channel 18. A first one-way valve 14 is provided between the first inhalation channel 12 and the filter 15, and a second one-way valve 17 is provided between the filter 15 and the second inhalation channel 18. The inhalation inflow component 11 and the exhalation discharge component 13 may be formed at the same place, but may instead be provided separately.

The handle component 1 will be described here by going through the procedure by which the user measures exhalation.

First, in the state in FIG. 1, the user grasps the handle component main body 4 in FIG. 2 (part of the handle component 1) in order to blow into the handle component 1, and places his mouth against the exhalation discharge component 13 of the mouthpiece 5. The user then first inhales, with his mouth pressed against the exhalation discharge component 13, in order to be ready to blow exhalation into the measurement device main body 3.

When the user inhales, air is brought into the handle component 1 through the inhalation holes 6 of the handle component main body 4. The air that is brought in goes through the first inhalation channel 12, passes the first one-way valve 14, and flows into the filter 15.

Here, the inhalation holes 6 are formed on the side where the end 2a of the tube 2 is connected to the handle component main body 4, that is, to a curved face 16, so that the inhalation holes 6 will not be blocked off by the user's hand when the user holds the handle component main body 4 in his hand. The curved face 16 is formed in a tapered shape from the end 2a side of the tube 2 toward the other end 2b side, so that it widens from the cylindrical part 8 side to the outer peripheral part 20 side.

This configuration allows air to flow smoothly into the handle component 1, and results in a device that is more convenient to use, with no need for re-measurement or the like.

Next, the air that has flowed into the filter 15 has the nitrogen monoxide in it removed by a nitrogen monoxide remover disposed in the filter 15.

The air from which the nitrogen monoxide has been removed passes the second one-way valve 17, goes through the second inhalation channel 18, flows into the inhalation inflow component 11 of the mouthpiece 5, and is inhaled into the body of the user. After this, when the user exhales into the exhalation discharge component 13 of the mouthpiece 5, his exhalation flows into the discharge channel 19.

The exhalation that the user has blown out from the exhalation discharge component 13 of the mouthpiece 5 goes through the discharge channel 19, then through the tube 2 connected to the connector 7, and flows into the measurement device main body 3, where the nitrogen monoxide in the exhalation is measured.

The discharge channel 19 and the second inhalation channel 18 are formed at the same place, but may instead be provided separately.

Thus, the user holds the handle component 1 in his hand and blows into it, in the course of which the user pulls the handle component 1 into his mouth and blows his exhalation into it.

Measurement Device Main Body 3

Figure 3:
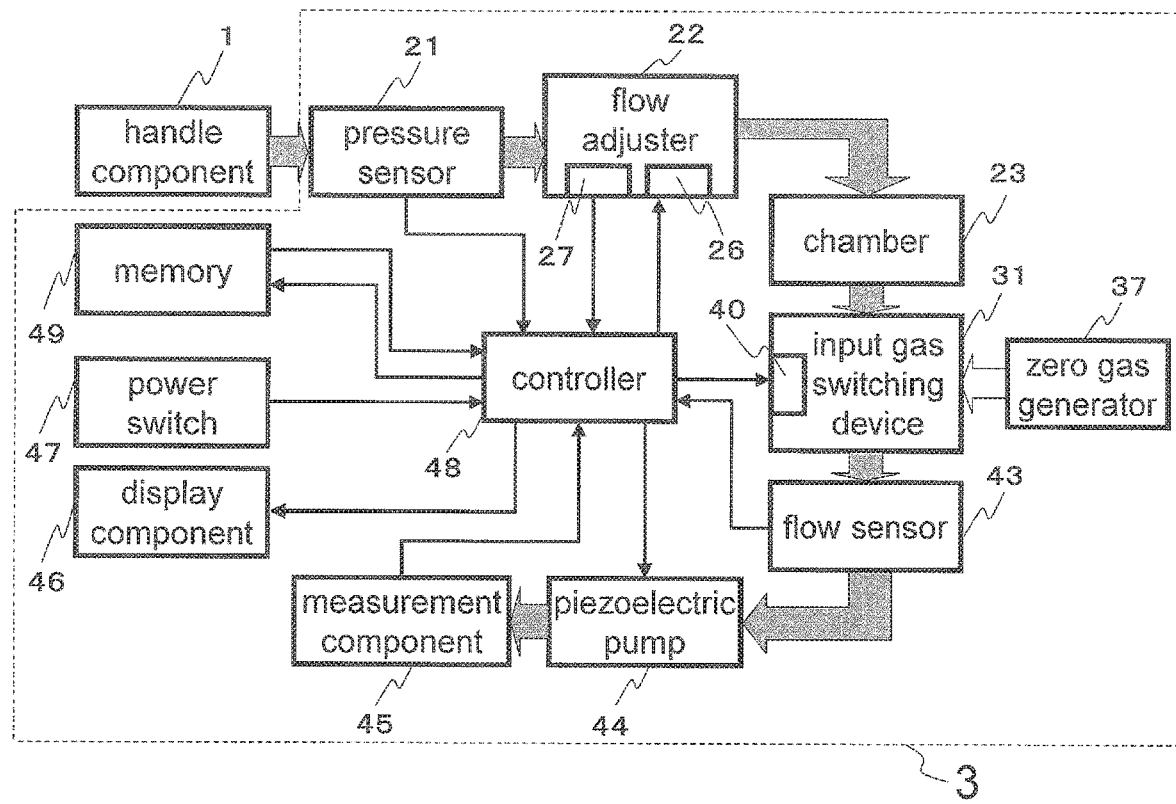
FIG. 3 is a control block diagram of an exhalation measurement device.

FIG. 3 is a block diagram of the configuration of the exhalation measurement device in this implementation. As shown in FIG. 3, the measurement device main body 3 in this implementation comprises a pressure sensor 21, a flow adjuster 22, a chamber 23, a zero gas generator 37, an input gas switching device 31, a flow sensor 43, a piezoelectric pump 44, a measurement component 45, a display component 46, a power switch 47, a memory 49, and a controller 48.

Pressure Sensor 21 and Flow Adjuster 22

The pressure sensor 21 measures the pressure of exhalation that flows from the handle component 1 into the measurement device main body 3 via the tube 2, and whether or not exhalation has been blown in can be determined by the pressure sensor 21.

Figure 4:
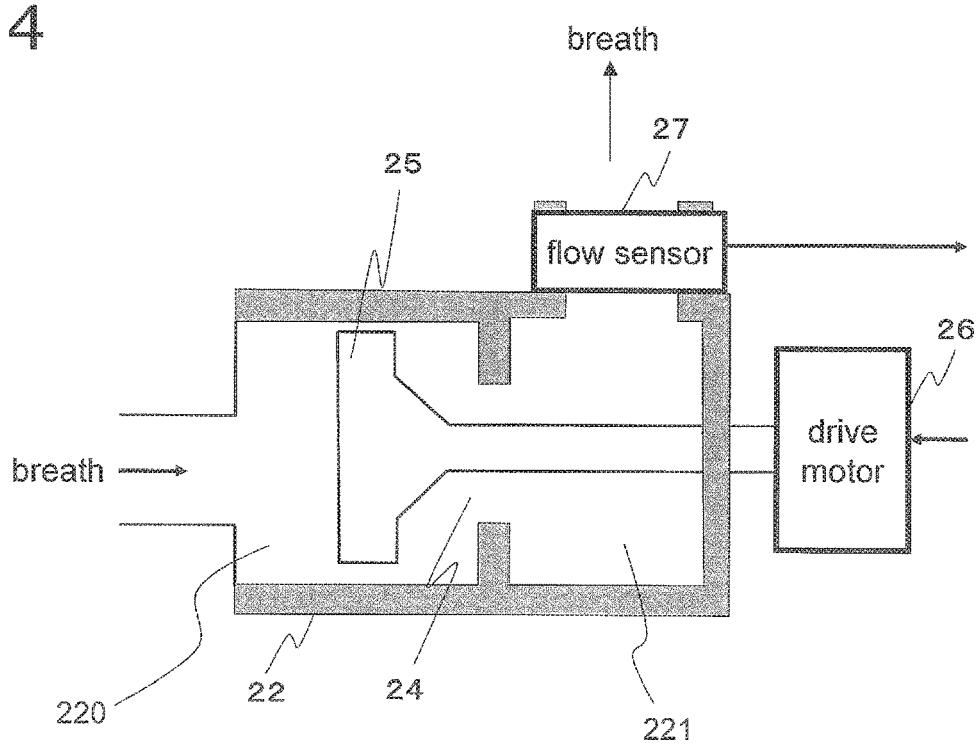
FIG. 4 is a cross section of the chamber of an exhalation measurement device.

FIG. 4 is a diagram of the configuration of the flow adjuster 22. The flow adjuster 22 adjusts the flow of the exhalation which flows in and supplies the exhalation to the chamber 23. The flow adjuster 22 has an exhalation inflow component 220 where the exhalation flows in, an exhalation outflow component 221 where the exhalation flows out, a valve hole 24 that allows the exhalation inflow component 220 to communicate with the exhalation outflow component 221, a drive valve 25 that can open and close the valve hole 24, a drive motor 26, and a flow sensor 27 provided on the outflow side to the chamber 23. The drive valve 25 is configured to be driven by the drive motor 26, and the flow sensor 27 monitors the exhalation quantity downstream of the flow adjuster 22. The drive motor 26 is controlled by the controller 48 on the basis of the sensing result by the pressure sensor 21 and the flow sensor 27.

Specifically, the exhalation supplied from the handle component 1, through the tube 2, to the measurement device main body 3 is then supplied to the chamber 23 in a state in which the flow has been adjusted by the pressure sensor 21 and the flow adjuster 22 shown in FIGS. 3 and 4.

More specifically, first the pressure sensor 21 senses the pressure of the exhalation, and detects the inflow of the exhalation. Then, the flow adjuster 22 reduces the aperture of the valve hole 24 with the drive valve 25 if the flow of exhalation sensed by the flow sensor 27 is large, and increases the aperture of the valve hole 24 with the drive valve 25 if the flow of exhalation sensed by the flow sensor 27 is small. This control stabilizes the flow of exhalation to the chamber 23.

Chamber 23

Figure 5:
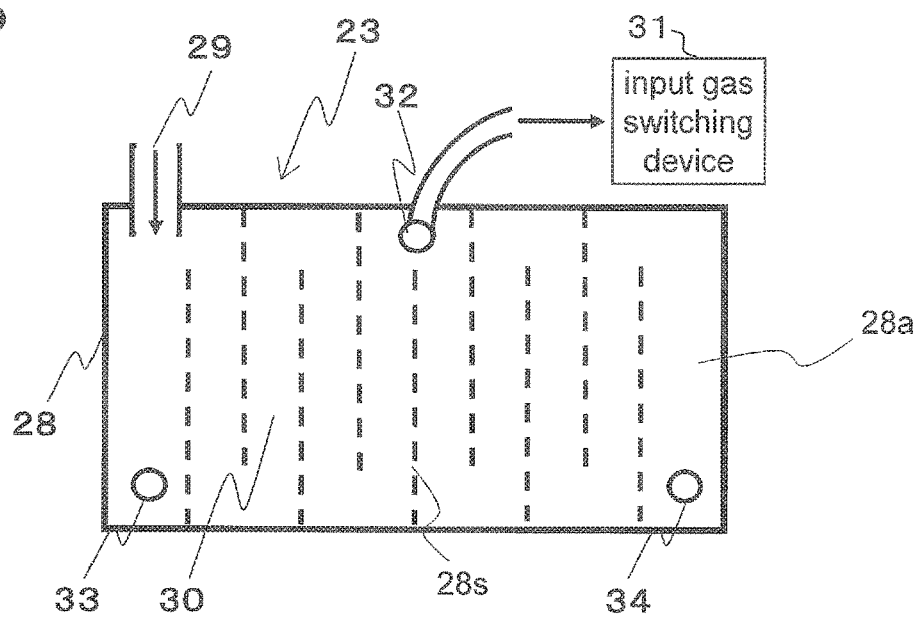
FIG. 5 is a cross section of the flow adjuster of an exhalation measurement device.

FIG. 5 is a simplified view of the configuration of the chamber 23.

As shown in FIG. 5, the chamber 23 is provided with an inlet 29 from the flow adjuster 22 side, at one end of a container 28. Also, an undulating path 30 is formed inside this container 28, and an outlet 32 to the input gas switching device 31 shown in FIG. 3 is formed in the middle portion of this undulating path 30. Intake/discharge holes 33 and 34 are formed on the starting point and end point sides, respectively, of the undulating path 30.

The container 28 is substantially cuboid, and has substantially rectangular, opposing flat faces, and side faces provided in between these two flat faces and perpendicular to them.

One of the opposing flat faces of the container 28 is placed on the inner face of the housing of the measurement device main body 3. In FIG. 5, the flat face not touching the inner face of the housing out of the opposing flat faces of the container 28 is shown as 28a. The intake/discharge holes 33 and 34 are formed by through-holes that go through this flat face 28a. Also, walls 28s are formed substantially perpendicular to the flat face 28a, and the undulating path 30 is formed by these walls 28s.

Since the intake/discharge holes 33 and 34 are linked to the outside of the measurement device main body 3, the inside of the chamber 23 is always open to the air.

Input Gas Switching Device 31

Figure 6:
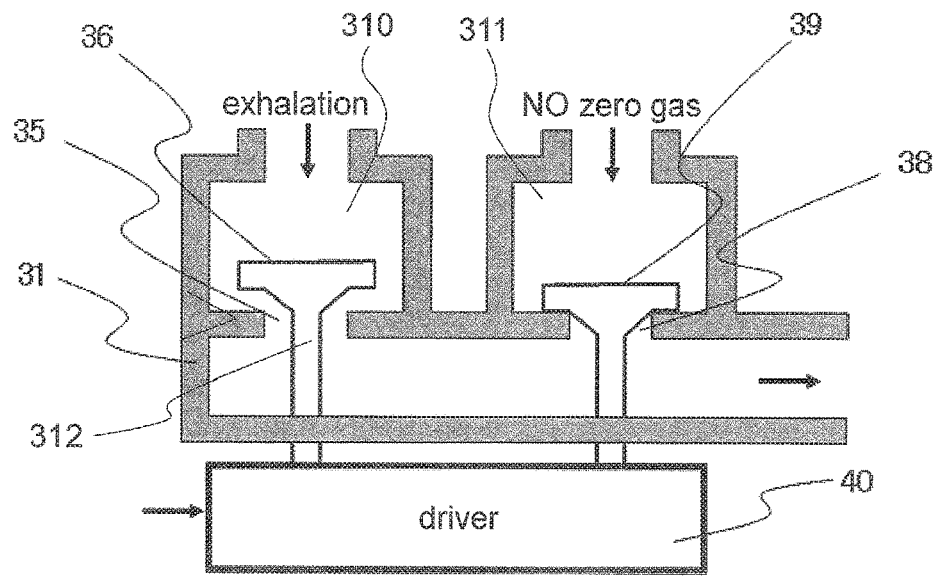
FIG. 6 is a cross section of an input gas switching device of an exhalation measurement device.

FIG. 6 is a simplified view of the configuration of the input gas switching device 31.

As shown in FIG. 6, the input gas switching device 31 has an exhalation inflow component 310, a zero gas inflow component 311, an outflow component 312, a valve hole 35, a drive valve 36, a valve hole 38, a drive valve 39, and a driver 40.

Exhalation flows into the exhalation inflow component 310 from the outlet 32 of the chamber 23. NO zero gas flows into the zero gas inflow component 311 from the zero gas generator 37 (discussed below). The zero gas or exhalation that has flowed in flows out from the outflow component 312 to the flow sensor 43 (discussed below) side.

The valve hole 35 allows the exhalation inflow component 310 to communicate with the outflow component 312. The drive valve 36 is able to open and close the valve hole 35, and is driven by the driver 40. The valve hole 38 allows the zero gas inflow component 311 to communicate with the outflow component 312. The drive valve 39 is able to open and close the valve hole 38, and is driven by the driver 40. The driver 40 is controlled by the controller 48, and drives the drive valve 36 and the drive valve 39.

Specifically, the valve hole 35 and the drive valve 36 are interposed in the channel in which exhalation is drawn in from the outlet 32 of the chamber 23, and the valve hole 38 and the drive valve 39 are interposed in the channel in which air is drawn out from the zero gas generator 37 shown in FIG. 7. The NO zero gas from the zero gas generator 37 or the exhalation inside the chamber 23 can be selectively sent to the flow sensor 43 side by the drive valve 36 and the drive valve 39 being driven by the driver 40.

Zero Gas Generator 37

Figure 7A:
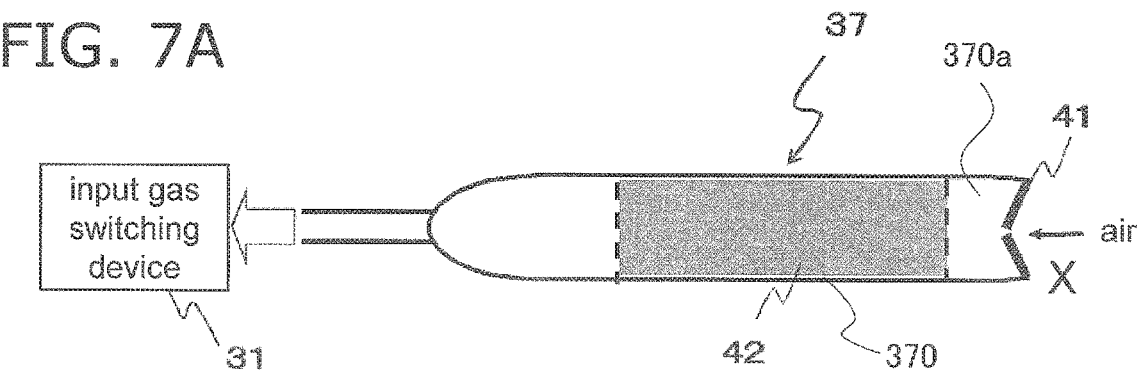
FIG. 7A is a cross section of a zero gas generator of an exhalation measurement device.

FIG. 7A is a simplified view of the configuration of the zero gas generator 37.

As shown in FIG. 7A, the zero gas generator 37 has a container 370, a filter 42 disposed in the container 370, and a one-way valve 41 disposed in an opening 370a on the opposite side of the container 370 from the input gas switching device 31. The one-way valve 41 opens only during inhalation. The filter 42 is provided downstream from the one-way valve 41 in the air intake direction, and removes nitrogen monoxide.

Figure 7B:
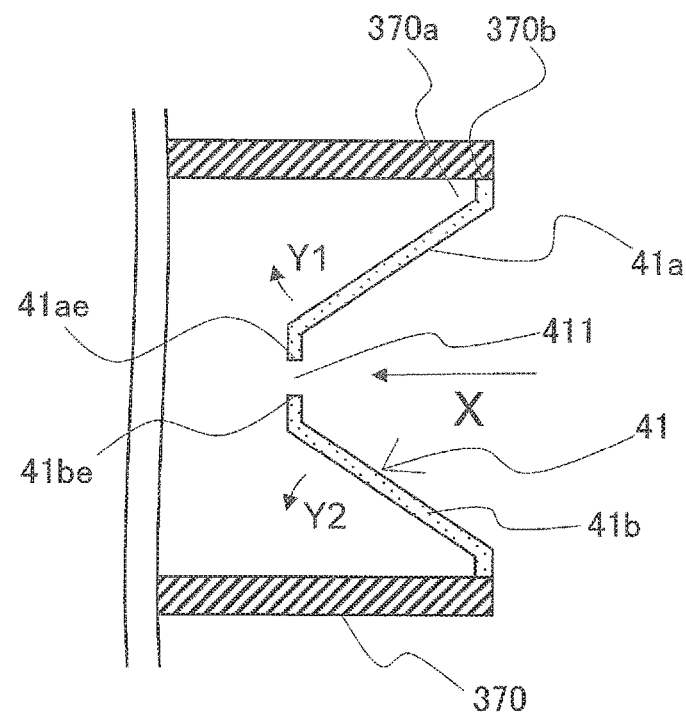
FIG. 7B is a detailed enlargement of FIG. 7A.
Figure 7C:
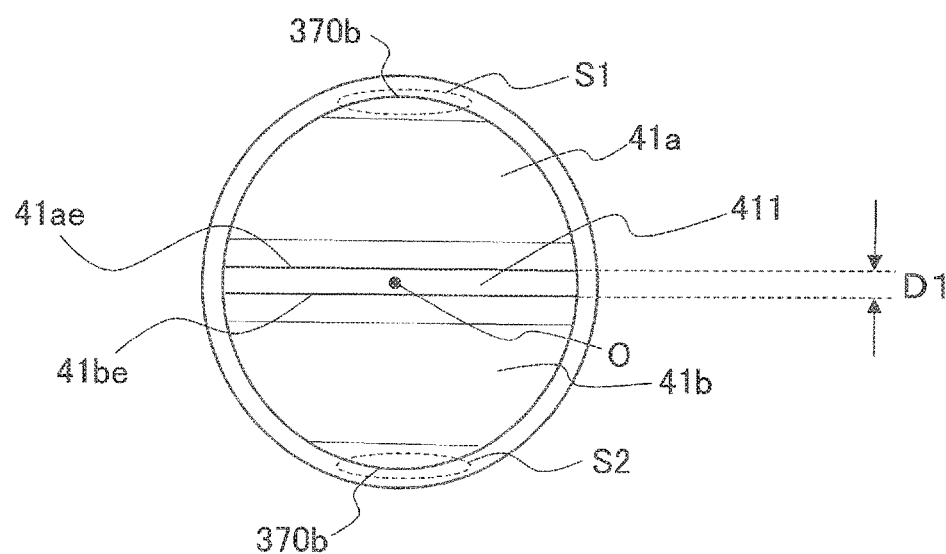
FIG. 7C is a rear view of FIG. 7B as seen in the arrow X direction.

FIG. 7B is a detail view of the area of the zero gas generator 37 near the one-way valve 41. FIG. 7C shows the zero gas generator 37 in the arrow X direction shown in FIG. 7A.

As shown in FIG. 7B, the opening 370a is formed at the end of the container 370 on the opposite side from the input gas switching device 31, and the one-way valve 41 is disposed so as to block off this opening 370a. The one-way valve 41 is formed from rubber or the like. As shown in FIG. 7C, the one-way valve 41 has a first portion 41a and a second portion 41b that are semicircular when viewed in the X direction. The first portion 41a and the second portion 41b are bonded to the edge 370b of the opening 370a in the middle portion of the curved outer periphery, and are disposed at an angle so as to gradually move closer together toward the inside of the container 370. The bonded portion of the first portion 41a and the edge 370b is indicated by S1 in FIG. 7C, and the bonded portion of the second portion 41b and the edge 370b is indicated by S2 in FIG. 7C.

A slit 411 is formed between the end 41ae of the first portion 41a on the inside of the container 370 and the end 41be of the second portion 41b on the inside of the container 370. As shown in FIG. 7C, the slit 411 is formed along the diameter passing through the center O of the opening 370a.

When the piezoelectric pump 44 is operated and air is drawn in from the arrow X direction, the first portion 41a receives the flow of air, and its end 41ae side deforms so as to move to the wall side of the container 370 (in the arrow Y1 direction), while the second portion 41b receives the flow of air, and its end 41be side deforms so as to move to the wall side of the container 370 (in the arrow Y2 direction). Deformation of the first portion 41a and the second portion 41b widens the opening, and air is drawn into the filter 42.

Meanwhile, even if the pressure has risen on the inside of the container 370, since the first portion 41a and the second portion 41b are disposed so that the distance between them narrows from the outside of the container 370 toward the inside, the spacing of the end 41ae and the end 41be does not widen, and in fact narrows, which impedes the flow of gas to the outside.

Since the slit 411 is formed in the zero gas generator 37 in this implementation, even if no air is drawn into the zero gas generator 37, the filter 42 will be in contact with the air and its performance will gradually deteriorate, but the spacing of the slit 411 is adjusted so that the NO removal effect of the filter can be sustained for a certain length of time.

Flow Sensor 43, Piezoelectric Pump 44, and Measurement Component 45

As shown in FIG. 3, the piezoelectric pump 44 is provided via the flow sensor 43 on the downstream side of the input gas switching device 31 shown in FIG. 6. The flow sensor 43 measures the flow of gas that is drawn in when the piezoelectric pump 44 is operated.

Figure 8A:
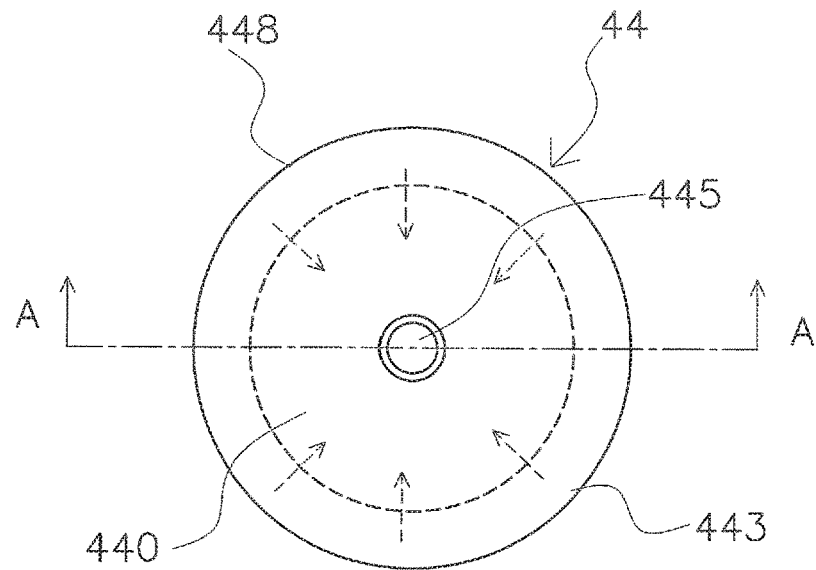
FIG. 8A is a simplified plan view of the piezoelectric pump in an exhalation measurement device.
Figure 8B:
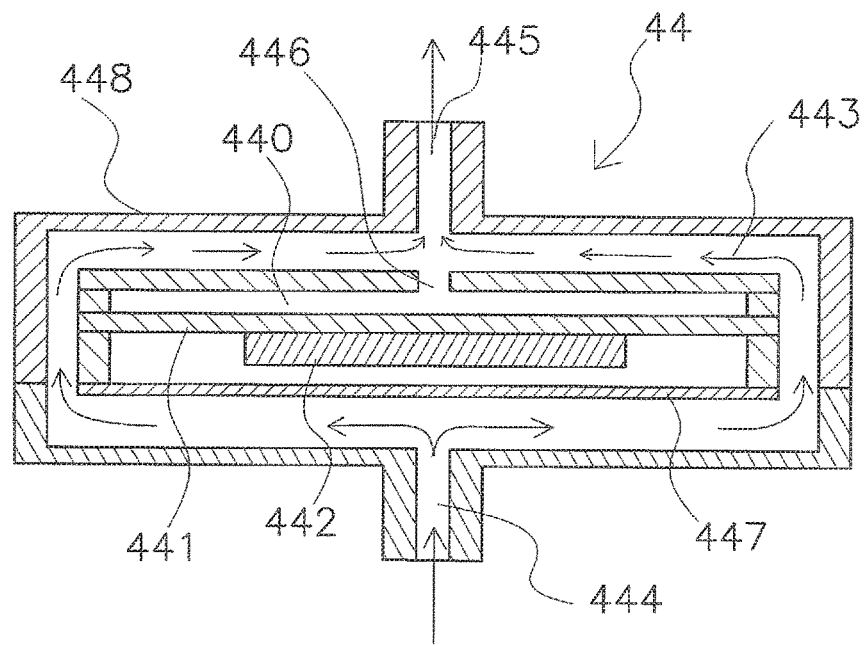
FIG. 8B is a cross section along the AA arrow in FIG. 8A.

FIG. 8A is a simplified plan view of the piezoelectric pump 44. FIG. 8B is a cross section along the AA line in FIG. 8B. As shown in FIGS. 8A and 8B, the piezoelectric pump 44 has a substantially cylindrical housing 448. A gas outlet 445 is provided in the center of the upper face of the housing 448, and a gas inlet 444 is provided in the center of the bottom face of the housing 448. The inlet 444 is connected to the input gas switching device 31 via the flow sensor 43. The outlet 445 is connected to the measurement component 45.

The piezoelectric pump 44 also comprises a pump chamber 440 disposed in the center of the interior of the housing 448, a diaphragm 441 that forms part of the pump chamber 440 (the bottom face side), a piezoelectric element 442 provided on the lower side of the diaphragm 441 and the outside of the pump chamber 440, a cover 447 disposed so as to cover the piezoelectric element 442 from the lower side, and a channel 443 that is formed around the cover 447 and the pump chamber 440 and communicates with the pump chamber 440 via a hole 446. More precisely, the channel 443 is formed between the pump chamber 440 and the housing 448, and between the housing 448 and the cover 447, on the upper face side, the side face sides, and the lower face side of the cover 447 and the pump chamber 440.

The diaphragm 441 is vibrated by vibrations from the piezoelectric element 442, and gas moves through the channel 443 from the inlet 444 toward the outlet 445 as the pump chamber 440 increases or decreases in volume (see the arrows in FIGS. 8A and 8B).

With the piezoelectric pump 44, since the vibration of the piezoelectric element 442 provides a gas pumping function, vibration of the piezoelectric element 442 sends exhalation or zero gas into the measurement component 45. This will be discussed in detail below, but examples of parameters that are inputted in order to actuate the piezoelectric pump 44 include the vibration frequency at which the piezoelectric element 442 vibrates, the applied voltage, and the duty ratio of the applied voltage. The accuracy of the flow sent to the measurement component 45 can be improved, and measurement can be performed more accurately, by setting these parameters to the proper values. The control for obtaining the proper values for these parameters will be discussed below.

The measurement component 45 is provided downstream from the piezoelectric pump 44. With this measurement component 45, the amount of nitrogen monoxide is sensed and the result is displayed on the display component 46.

As shown in FIG. 3, the above-mentioned the pressure sensor 21, the drive motor 26, the flow sensor 27, the driver 40, the flow sensor 43, the piezoelectric pump 44, the measurement component 45, the display component 46, and the power switch 47 are connected to the controller 48.

Controller 48

Figure 9:
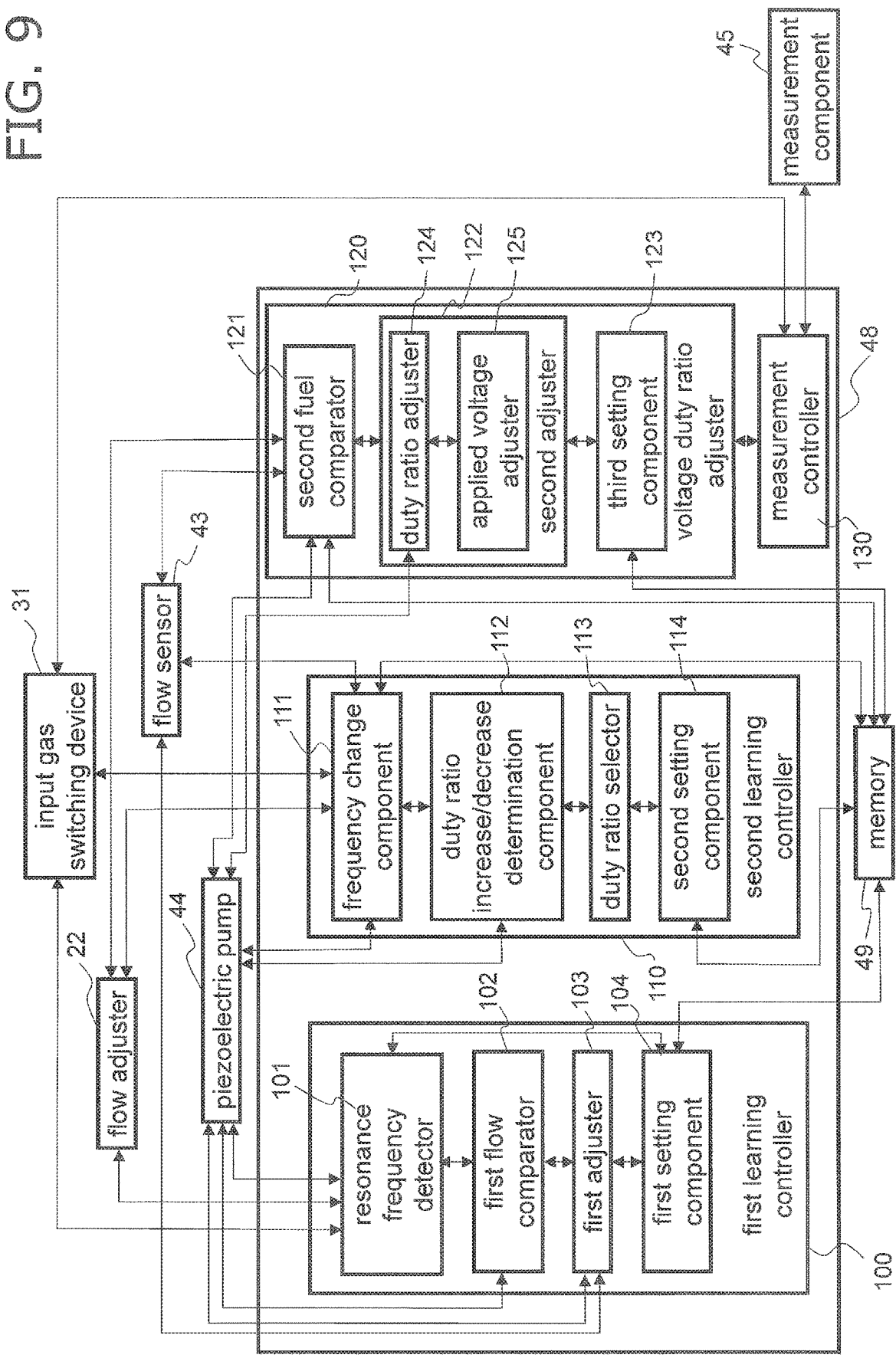
FIG. 9 is a control block diagram of an exhalation measurement device.

FIG. 9 is a block diagram of the configuration related to control of the piezoelectric pump 44 in the controller 48.

The controller 48 of the exhalation measurement device in this implementation has a first learning controller 100, a second learning controller 110, a voltage duty ratio adjuster 120, and a measurement controller 130 in order to select and set the vibration frequency, the drive voltage, and the duty ratio, which are parameters for actuating the piezoelectric pump 44 in the measurement of the nitrogen monoxide concentration by the measurement component 45. In FIG. 9, the components related to control other than the piezoelectric pump 44 are not shown.

First Learning Controller 100

The first learning controller 100 calculates the drive voltage and a first drive frequency for operating the piezoelectric pump 44. The first learning controller 100 has a resonance frequency detector 101, a first flow comparator 102, a first adjuster 103, and a first setting component 104.

The resonance frequency detector 101 detects the resonance frequency of the piezoelectric element of the piezoelectric pump 44 by varying the frequency in a state in which a specific voltage has been applied.

The first flow comparator 102 compares a target flow to the flow sensed by the flow sensor 43 when the piezoelectric pump 44 is operated using the above-mentioned specific voltage and resonance frequency values. When the piezoelectric pump 44 is operated, this results in a state in which NO zero gas from the zero gas generator 37 is sent by the input gas switching device 31 to the piezoelectric pump 44.

The first adjuster 103 adjusts the value of the specific application voltage so that the flow sensed by the flow sensor 43 becomes the target flow, on the basis of the comparison result of the first flow comparator 102.

The first setting component 104 sets the resonance frequency as a first drive frequency, sets the adjusted application voltage as the drive application voltage, and stores these in the memory 49.

Second Learning Controller 110

The second learning controller 110 selects and sets a second drive frequency and a drive duty ratio on the basis of the first drive frequency and the drive application voltage.

The second learning controller 110 has a frequency change component 111, a duty ratio increase/decrease determination component 112, duty ratio selector 113, and a second setting component 114.

The frequency change component 111 changes the first drive frequency at a specific frequency interval while changing the duty ratio of the drive application voltage to keep the flow constant, on the basis of the flow sensed by the flow sensor 43.

The duty ratio increase/decrease determination component 112 determines an increase or decrease in the duty ratio accompanying a change in frequency by the frequency change component 111.

The duty ratio selector 113 selects the smallest duty ratio on the basis of the determined increase or decrease in the duty ratio.

The second setting component 114 sets as a second drive frequency the frequency at which the duty ratio was selected by the duty ratio selector 113, and sets the selected duty ratio as a drive duty ratio.

Voltage Duty Ratio Adjuster 120

The voltage duty ratio adjuster 120 adjusts the drive duty ratio and the drive application voltage on the basis of the second drive frequency so that the sensed flow will become the target flow when the flow sensed by the flow sensor 43 is different from the target flow after the second drive frequency, the drive application voltage, and the drive duty ratio have been set.

The voltage duty ratio adjuster 120 has a second fuel comparator 121, a second adjuster 122, and a third setting component 123.

During measurement, the second fuel comparator 121 compares the target flow value with the flow of exhalation flown from within the chamber 23 by the piezoelectric pump 44 operated using the second drive frequency, the drive application voltage, and the drive duty ratio.

The second adjuster 122 has an applied voltage adjuster 125 that adjusts applied voltage so as to attain the target flow, and a duty ratio adjuster 124 that adjusts the duty ratio.

The third setting component 123 sets the adjusted drive application voltage and the drive duty ratio in the memory 49 as the new drive application voltage and drive duty ratio.

Measurement Controller 130

The measurement controller 130 controls the input gas switching device 31, the zero gas generator 37, the measurement component 45, and so forth during measurement. More specifically, after the concentration of nitrogen monoxide in the exhalation inside the chamber 23 is measured by the measurement component 45, the input gas switching device 31 is switched to the zero gas generator 37 side, and the nitrogen monoxide concentration (blank value) in the NO zero gas is measured, after which the blank value is subtracted from the nitrogen monoxide concentration in the exhalation to calculate the nitrogen monoxide concentration.

2. Operation

Figure 10:
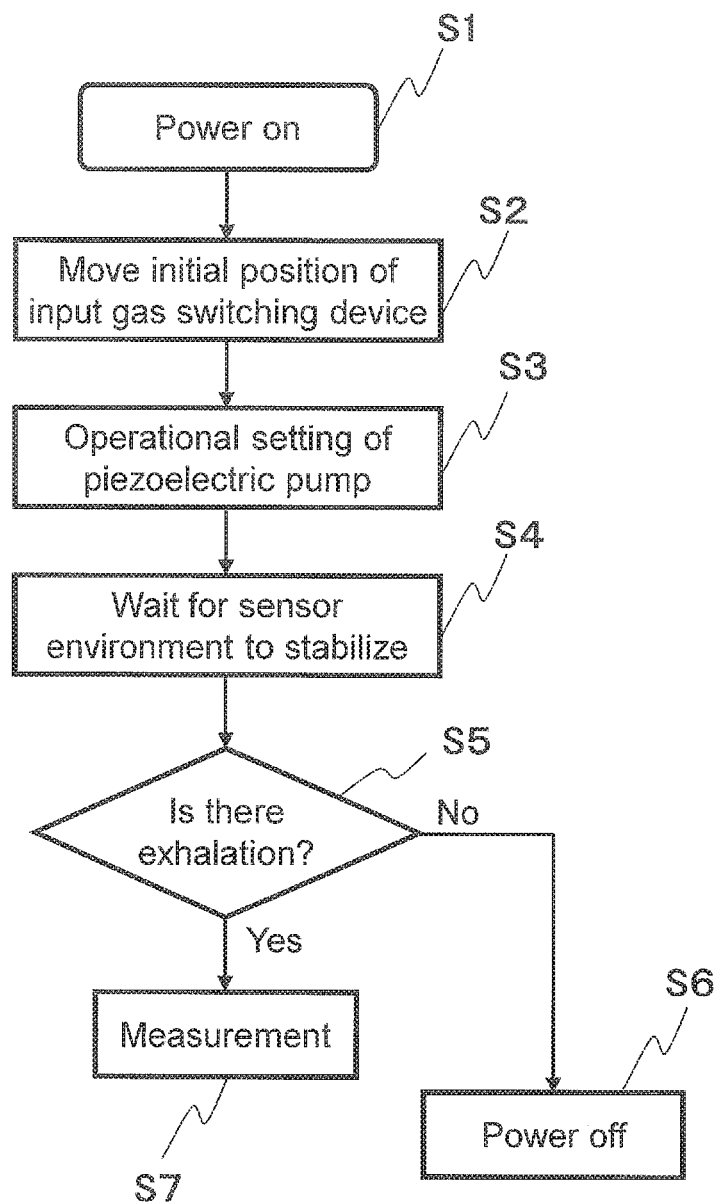
FIG. 10 is an operational flowchart of an exhalation measurement device.

FIG. 10 is a flowchart of the exhalation measurement device in this implementation.

With the above configuration, to perform exhalation measurement, the first thing is to turn on the power switch 47 in FIG. 3 (S1 in FIG. 10).

This causes the controller 48 to put the input gas switching device 31 shown in FIG. 6 in its initial state (S2 in FIG. 10). This initial state is one in which the drive valves 36 and 39 are driven by the driver 40, the valve hole 35 is closed by the drive valve 36, and the valve hole 38 is opened.

Next, the controller 48 performs operational setting on the piezoelectric pump 44 (an example of a first learning control step).

Piezoelectric Pump Operational Setting S3
(Example of First Learning Control Step)

Figure 11:
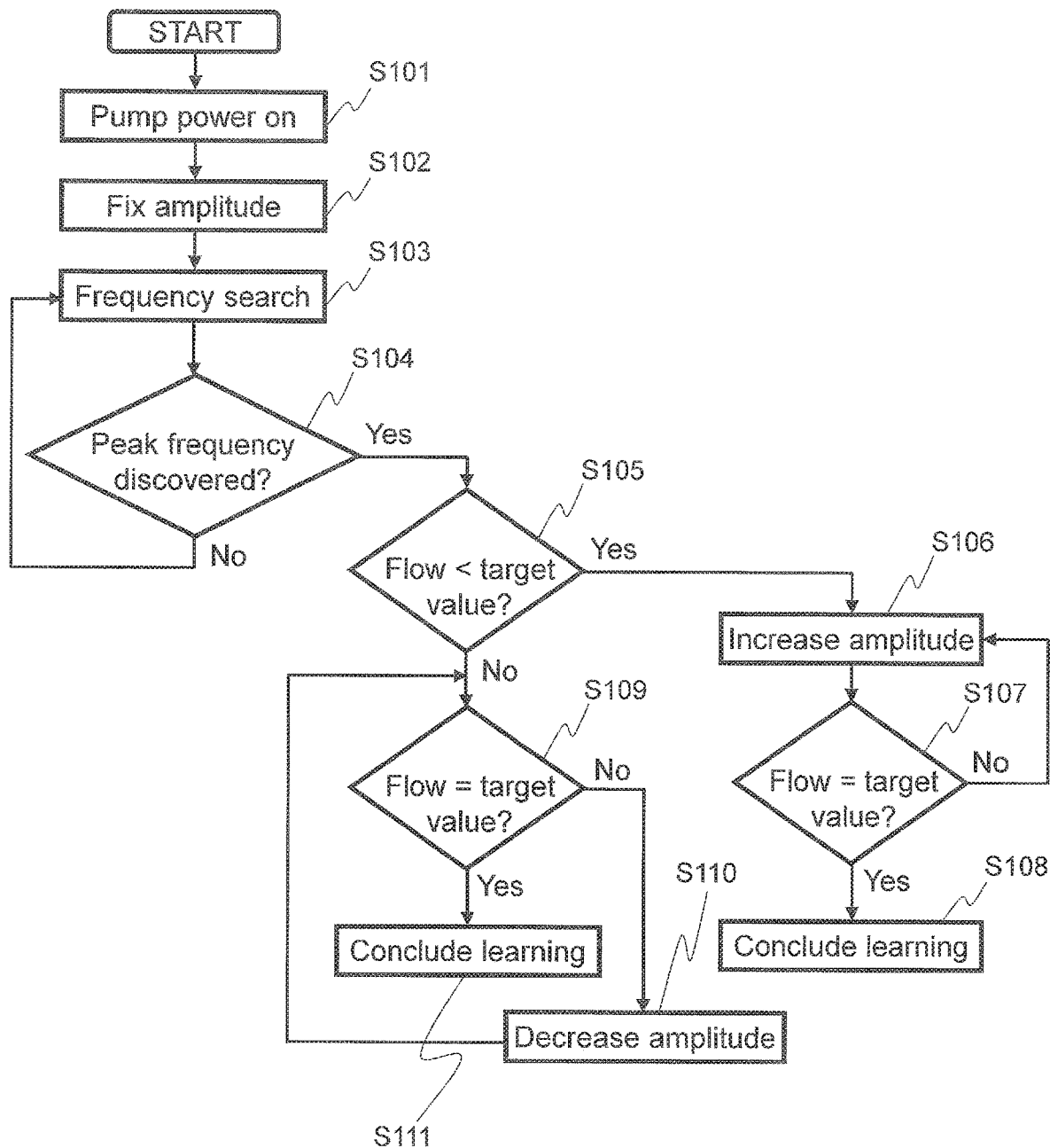
FIG. 11 is an operational flowchart of an exhalation measurement device.

The operational setting of the piezoelectric pump 44 will now be described in detail through reference to FIG. 11. FIG. 11 is a flowchart of the control of operational setting of the piezoelectric pump 44 of the exhalation measurement device in this implementation.

The piezoelectric pump 44 itself may be configured so that a piezoelectric element (not shown) is vibrated at 24 to 28 kHz, for example, and exhalation is transported by this vibrational force.

When this piezoelectric pump 44 is used, first, the resonance frequency detector 101 of the controller 48 switches on the power to the piezoelectric pump 44 (S101 in FIG. 11), then sets the voltage applied to the piezoelectric element to 6 V, for example (an example of a specific applied voltage) (S102 in FIG. 11), and performs a frequency search at a fixed amplitude (S103 in FIG. 11).

In this frequency search, the above-mentioned 6 V and 24 to 28 kHz are successively supplied to the piezoelectric element at an interval of 256 Hz, and the resonance frequency detector 101 roughly pre-selects the frequency at which this piezoelectric element will resonant. Next, another 6 V is successively supplied at a finer interval than 256 Hz (such as 20 Hz), over the range of 256 Hz above and below this roughly pre-selected frequency, and the frequency at which this piezoelectric element will resonate is selected.

Once the frequency at which the piezoelectric element will resonate has been selected by this frequency search (S104 in FIG. 11), the first flow comparator 102 then senses the flow with the flow sensor 43. Since the valve hole 38 shown in FIG. 6 is open at this point, when the piezoelectric pump 44 is driven, air is drawn in by the piezoelectric pump 44 through the valve hole 38 and the one-way valve 41 of the zero gas generator 37, and the flow at this point is sensed by the flow sensor 43.

The first flow comparator 102 detects whether or not the flow sensed by the flow sensor 43 is less than 3 mL/second (an example of a first target flow), which is the target flow (S105 in FIG. 11).

If the flow is less than the target flow of 3 mL/second, the first adjuster 103 raises the voltage applied to the piezoelectric element from the above-mentioned 6 V (S105 and S106 in FIG. 11). After this, the first flow comparator 102 again determines whether or not the flow sensed by the flow sensor 43 is at the target value (S107 in FIG. 11).

Once the flow sensed by the flow sensor 43 reaches the target value, the first setting component 104 stores this applied voltage (an example of the drive application voltage) in the memory 49 (shown in FIG. 3) along with the frequency selected above (S104 in FIG. 11) (an example of a first drive frequency) (S107 and S108 in FIG. 11).

Meanwhile, in S105 in FIG. 11, if the flow is not less than the target value, the first flow comparator 102 again determines whether or not the flow and the target value are the same, and if they are different, the first adjuster 103 lowers the voltage applied to the piezoelectric element from the above-mentioned 6 V (S109 and S110 in FIG. 11). Also, in S109 in FIG. 11, if the flow and the target value are the same, the first setting component 104 stores this applied voltage (an example of the drive application voltage) in the memory 49 shown in FIG. 3 along with the frequency selected above (S104 in FIG. 11) (an example of the first drive frequency) (S109 and S111 in FIG. 11).

The operational setting of the piezoelectric pump 44 in FIG. 10 (S3) is performed as above. The above-mentioned steps S101 to S104 correspond to an example of a resonance frequency sensing operation. Steps S105, S107, and S109 correspond to an example of a first flow comparison operation. Steps S106 and S110 correspond to an example of a first adjustment operation.

As discussed above, in the operational setting S3, the frequency (an example of the first drive frequency) and the applied voltage (an example of the drive application voltage) are set. The duty ratio of the applied voltage is set to 50%, and is set to the same value as the initial duty ratio of the operational setting of the piezoelectric pump in S205 (discussed below).

A measurement preparation completion state is then reached via the sensor environment stability waiting state (1 to 2 minutes) indicated by S4 in FIG. 10. More specifically, a message of "Blow into device" is displayed on the display component 46 by the controller 48 (S4 in FIG. 10).

Then, the controller 48 determines whether or not the pressure sensor 21 has sensed the pressure within the past three minutes, for example, after the display component 46 has displayed a command to blow into the device. That is, if no exhalation is blown in from the mouthpiece 5 within these three minutes, the pressure sensor 21 does not sense a pressure, and as a result the power is switched off (S5 and S6 in FIG. 10).

Also, if exhalation is blown in from the mouthpiece 5 within these three minutes, the pressure sensor 21 senses a pressure, and as a result the exhalation measurement operation is executed (S5 and S7 in FIG. 10).

The exhalation measurement operation (S7) will now be described through reference to FIG. 12.

Figure 12:
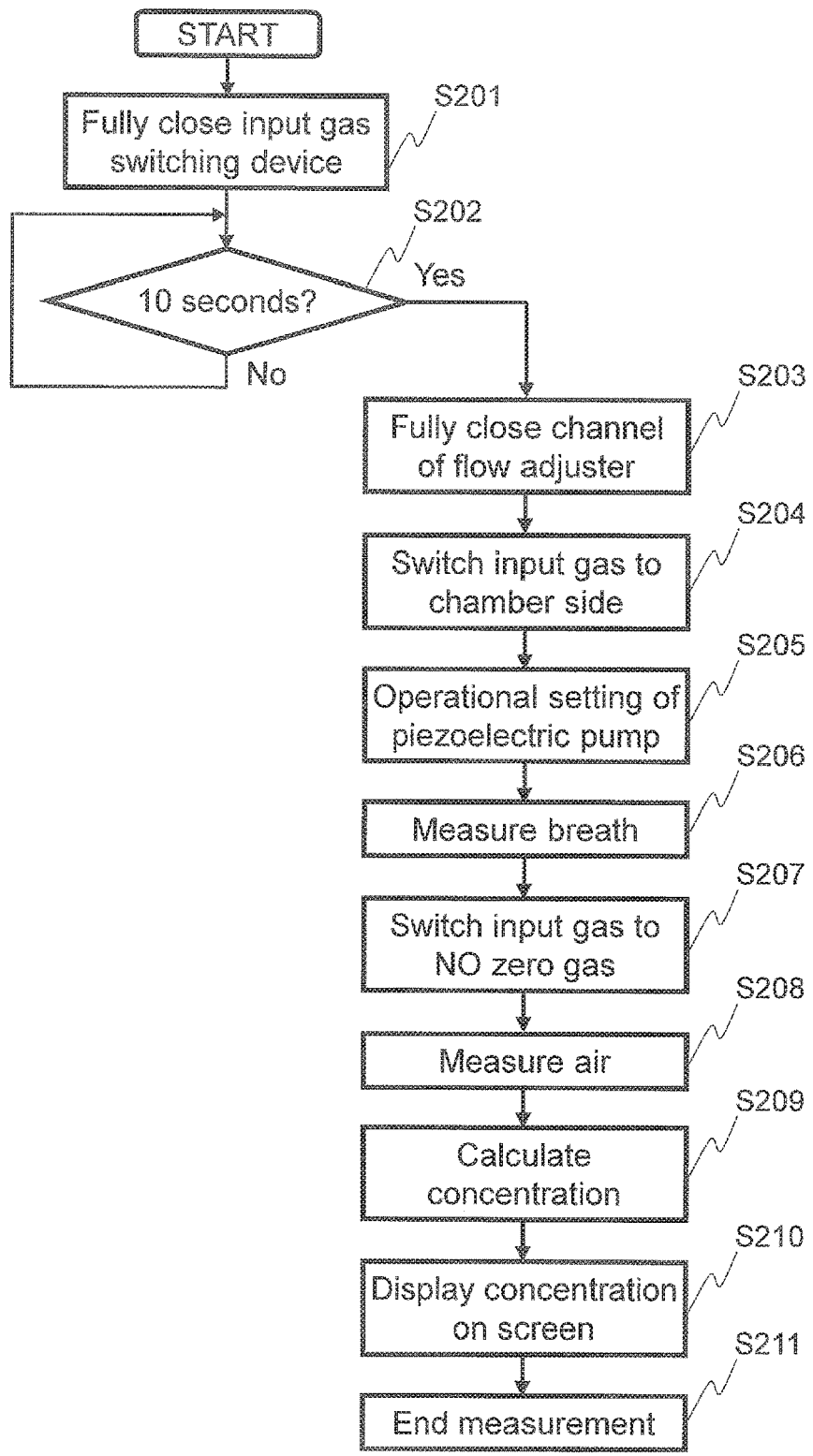
FIG. 12 is an operational flowchart of an exhalation measurement device.

During exhalation measurement operation, first, the controller 48 uses the driver 40 shown in FIG. 6 to drive the drive valves 36 and 39, and closes the valve holes 35 and 38 (S201 in FIG. 12).

This state is maintained for 10 seconds after pressure is sensed by the pressure sensor 21 (S202 in FIG. 12).

During the 10 seconds in which this state is maintained, the flow of exhalation is sensed by the flow sensor 27 provided to the flow adjuster 22, and the drive motor 26 is controlled on the basis of this result. This control results in exhalation being supplied to the chamber 23 at a constant flow via the flow adjuster 22 (see FIG. 4). More specifically, exhalation flows from the inlet 29 into the undulating path 30 in a state in which the flow is checked by the flow sensor 27. At this point, as discussed above, since the input gas switching device 31 is in a fully closed state, the outlet 32 of the chamber 23 is in a closed state, and part of the exhalation that flowed into this chamber 23 now flows out from the intake/discharge holes 33 and 34. That is, the air remaining in the chamber 23 is pushed out by the exhalation that was blown in, and consequently the inside the chamber 23 is filled with exhalation.

Once 10 seconds has elapsed since pressure was sensed by the pressure sensor 21, the controller 48 closes off the valve hole 24 of the flow adjuster 22 with the drive valve 25 (S203 in FIG. 12). That is, the valve hole 24 is closed off by the drive valve 25 when the controller 48 drives the drive motor 26.

The controller 48 then drives the drive valve 36 with the driver 40 of the input gas switching device 31, which opens up the valve hole 35 (S204 in FIG. 12). At this point the valve hole 38 of the input gas switching device 31 is in a closed state.

In this state the second learning controller 110 of the controller 48 performs operational setting of the piezoelectric pump 44 (an example of a second learning control step) (S205 in FIG. 12).

That is, the operational setting of the piezoelectric pump 44 was performed directly after the power switch 47 was switched on as discussed above (S3 in FIG. 10), but as time passes from that point on, the operational setting of the piezoelectric pump 44 is performed again in S205 in order to perform operational setting that is more precise than in the first learning control step.

Operational Setting S205 of Piezoelectric Pump 44 (Example of Second Learning Control Step)

The operational setting of the piezoelectric pump 44 (an example of a second learning control step) will now be described through reference to FIG. 13.

More specifically, the power to the piezoelectric pump 44 is already on (S101 in FIG. 11), and the voltage applied to the piezoelectric element is also set to a suitable value (such as 6 V) (an example of drive application voltage) during the operational setting in FIG. 11. Accordingly, the frequency is then switched to 20 Hz to reset the drive frequency to a proper level.

At this point, the drive frequency (an example of a first drive frequency) has already been set in FIG. 11, so the second learning controller 110 reselects a frequency while varying the duty ratio on the basis of the following steps S301 to S316 from within a range of 256 Hz above and below this frequency (an example of a specific region). Here, let us assume that the target flow during measurement is lower than that used in FIG. 11, and is set to 2 mL/second (an example of a second target flow), for example. The duty ratio of the voltage applied to the piezoelectric element is set to 50% of the maximum value during learning (S301 in FIG. 13).

The frequency change component 111 then senses the flow with the flow sensor 43. At this point, the valve hole 35 shown in FIG. 6 is open, so when the piezoelectric pump 44 is driven, the exhalation in the chamber 23 is drawn through the outlet 32 and the valve hole 35 of the input gas switching device 31 into the piezoelectric pump 44, and the flow at this point is sensed by the flow sensor 43.

Figure 13:
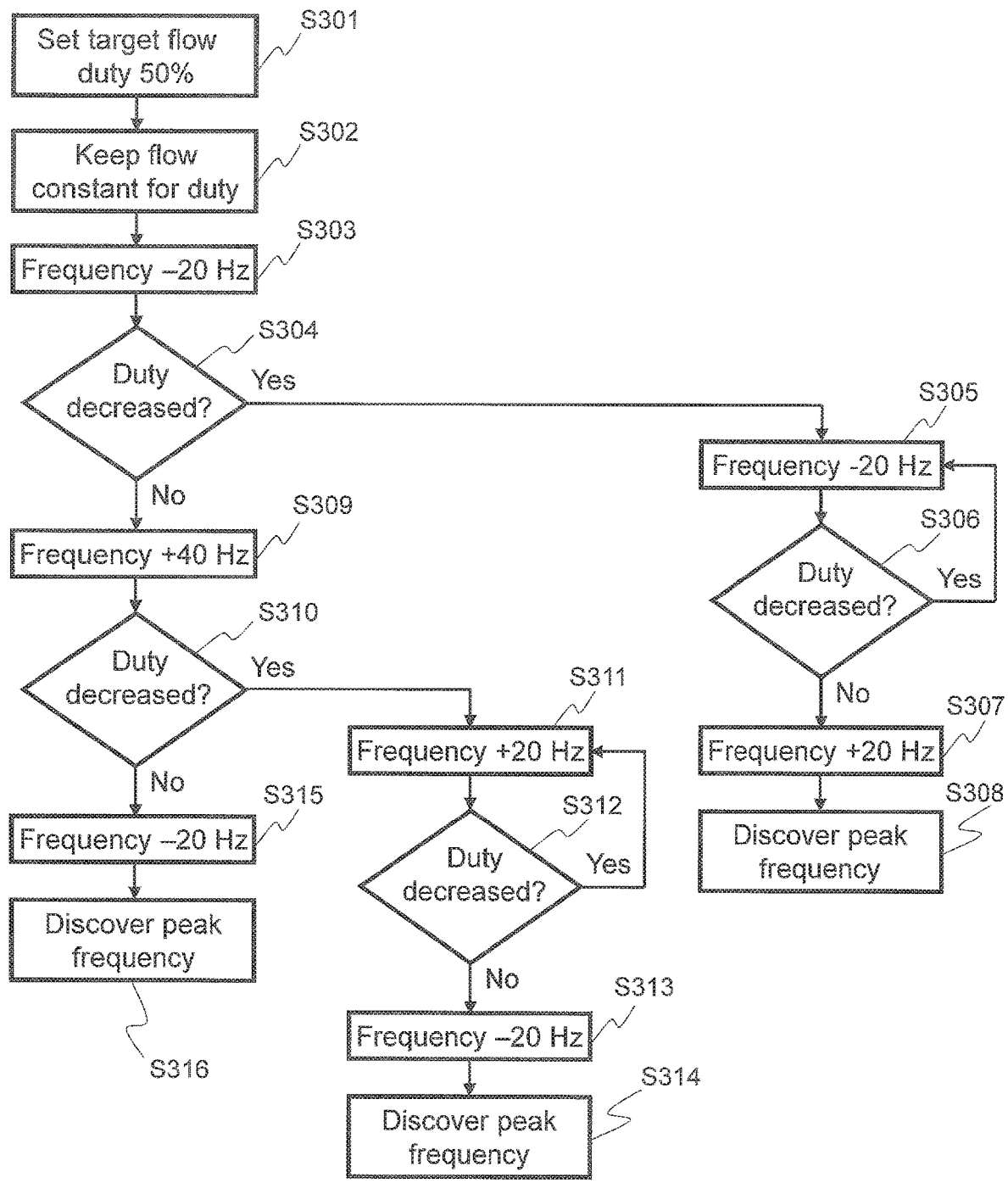
FIG. 13 is an operational flowchart of an exhalation measurement device.

The frequency change component 111 then changes the duty ratio to perform constant flow control (S302 in FIG. 13). For example, when the flow is smaller than the target flow, the frequency change component 111 increases the duty ratio 1% at a time, and conversely, when the flow is larger than the target flow, the duty ratio is decreased by 1% at a time until the target flow is reached. In this state (in which constant flow control is being performed), the frequency that was already set in FIG. 11 (an example of the first drive frequency) is changed up or down by a certain frequency (such as 20 Hz at a time), whereupon the duty ratio decreases as the peak frequency is approached. This is utilized to reset the peak frequency.

First, the frequency change component 111 changes the previously set frequency by −20 Hz (S303 in FIG. 13), the increase or decrease in the duty ratio at this time is determined by the duty ratio increase/decrease determination component 112, and it is determined whether or not the duty ratio has decreased (S304 in FIG. 13).

If the duty ratio has decreased, the frequency change component 111 changes the frequency by another −20 Hz, the duty ratio increase/decrease determination component 112 compares the duty ratio at this point with the duty ratio prior to the change (that is, the duty ratio at a frequency of +20 Hz) to determine if it has been decreased, and this series of operations is repeated (S305 and S306 in FIG. 13). The duty ratio selector 113 then selects the frequency setting prior to the duty ratio stopped decreasing as the frequency at which the piezoelectric element vibrates the most (an example of the second drive frequency), and the second setting component 114 records the frequency setting prior to the duty ratio stopped decreasing to the memory 49 in FIG. 3 (S307 and S308 in FIG. 13).

Specifically, the duty ratio selector 113 compares the duty ratio when the frequency has been changed by −20 Hz with the duty ratio at the frequency prior to this change, and if there was no decrease, the duty ratio at the frequency prior to the change is selected as the lowest duty ratio when the frequency is changed every range of 20 Hz. This frequency at the lowest duty ratio is then recorded by the second setting component 114 to the memory 49 as the frequency at which the piezoelectric element vibrates the most (an example of the second drive frequency).

If it is determined in S304 in FIG. 13 that there is no reduction in the duty ratio, the frequency change component 111 changes the current frequency by +40 Hz, that is, to a frequency that is +20 Hz over the frequency set in FIG. 11 (S309 in FIG. 13). The duty ratio increase/decrease determination component 112 then determines again whether the duty ratio at the changed frequency has decreased (S310 in FIG. 13).

If the duty ratio has decreased in S310 in FIG. 13, the frequency change component 111 changes the frequency by another +20 Hz, it is determined by the duty ratio increase/decrease determination component 112 whether the duty ratio has decreased, and this series of operations is repeated (S311 and S312 in FIG. 13). The duty ratio selector 113 selects the setting of the frequency before the duty ratio stopped decreasing as the frequency at which the piezoelectric element vibrates the most (an example of the second drive frequency), and the second setting component 114 records this to the memory 49 in FIG. 3 (S313 and S314 in FIG. 13).

Specifically, the duty ratio selector 113 compares the duty ratio when the frequency was changed by +20 Hz with the duty ratio at the frequency prior to the change, and if there was no decrease, the duty ratio at the frequency prior to the change is selected as the lowest duty ratio. The frequency when the duty ratio is lowest is then recorded by the second setting component 114 to the memory 49 as the frequency at which the piezoelectric element vibrates the most (an example of the second drive frequency).

If it is determined that there is no decrease in the duty in S310 in FIG. 13, the duty ratio selector 113 senses that the original frequency (the frequency obtained by subtracting 20 Hz from the frequency determined not to have decreased), that is, the frequency set in FIG. 11, is the frequency at which the piezoelectric element vibrates the most (an example of the second drive frequency), and the second setting component 114 records this to the memory 49 in FIG. 3 (S315 and S316 in FIG. 13).

The repetition of the above steps S305 and S306 in FIG. 13, or the repetition of the steps S311 and S312 in FIG. 12, must fall within the length of time discussed below, so the frequency change component 111 changes the frequency within a range of ±256 Hz from the frequency set in FIG. 11.

Also, when the frequency at which the piezoelectric element vibrates the most (an example of the second drive frequency) is recorded to the memory 49, the second setting component 114 also records the duty ratio at this frequency (an example of a drive duty ratio).

As discussed above, the optimal drive frequency (an example of the second drive frequency) and the duty ratio at the optimal drive frequency (an example of the drive duty ratio) are set as the operational setting of piezoelectric pump 44. The above-mentioned steps S301, S302, S303, S305, S309, and S311 correspond to an example of a frequency change operation. The above-mentioned steps S304, S306, S310, and S312 correspond to an example of a duty ratio increase/decrease determination operation. The above-mentioned steps S307, S308, S313, S314, S315, and S316 correspond to an example of a duty ratio selection operation.

Voltage Duty Ratio Control

Figure 14:
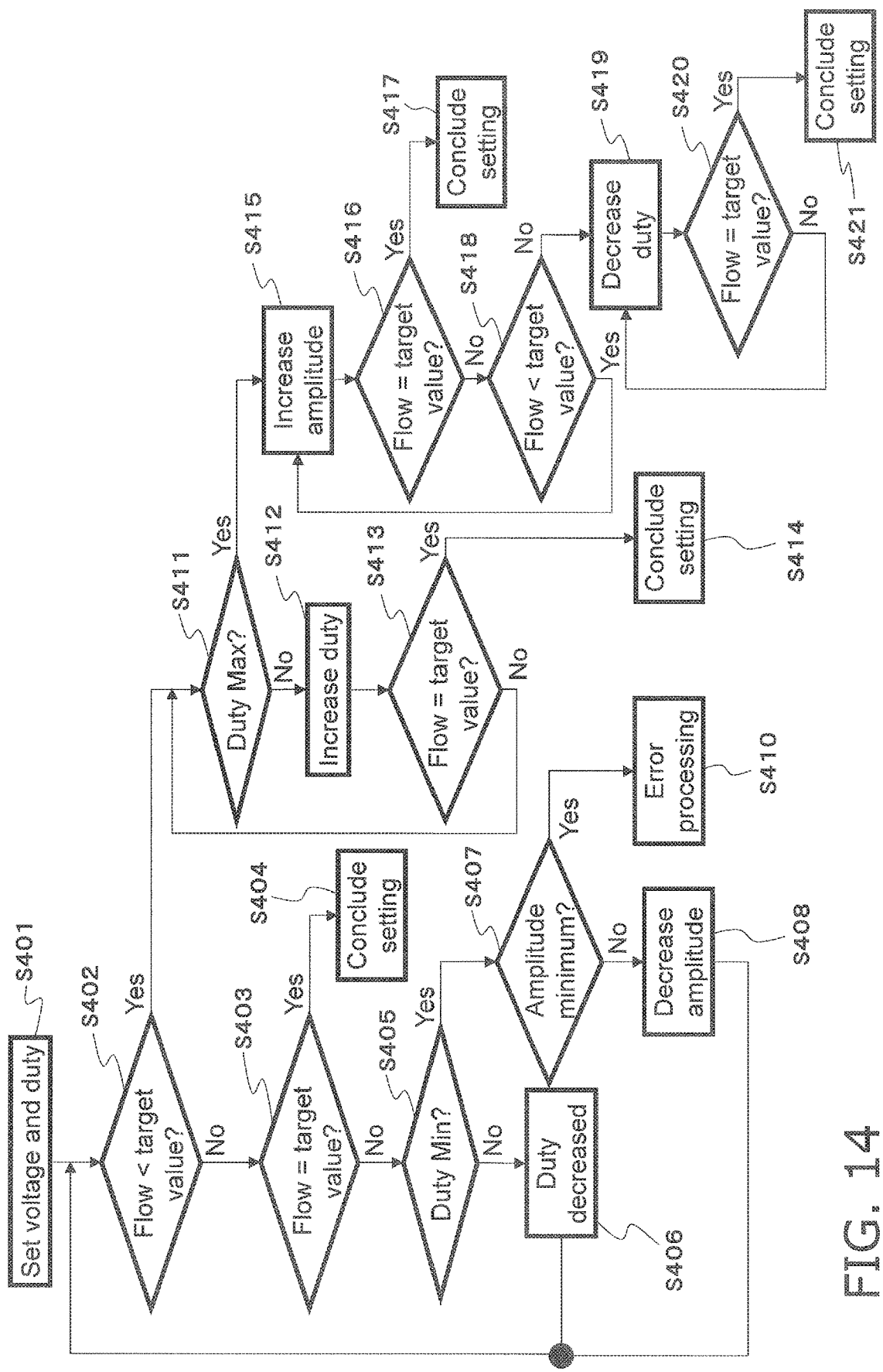
FIG. 14 is an operational flowchart of an exhalation measurement device.

When the optimal drive frequency (an example of the second drive frequency) is thus found as an operational setting, this optimal drive frequency is then fixed, and voltage duty ratio control is performed as shown in FIG. 14 to set the optimal drive voltage and the duty ratio for keeping the flow constant.

This voltage duty ratio control is executed by constantly monitoring the flow sensed by the flow sensor 43 during operation of the piezoelectric pump 44, even after the drive voltage and its duty ratio have been set, and is performed in order to keep the flow constant even when a change in the surrounding air flow, for example, causes the flow to be affected by turbulence.

For example, voltage duty ratio control is always executed when performing the exhalation measurement in S206 after the operational setting of the piezoelectric pump has been executed in S205, and if the flow does not match the target flow, control is performed so that the drive application voltage and the drive duty ratio will be adjusted such that the flow will match the target flow, and then measurement is performed by the measurement component 45.

More specifically, in this control, the optimal voltage to be applied to the piezoelectric element is found by the operational setting in FIG. 11 (an example of the first learning control step), and the duty ratio is found by the operational setting in FIG. 13 (an example of the second learning control step), so first the controller 48 sets the voltage applied to the piezoelectric element and the duty ratio to these values (S401 in FIG. 14).

Next, the second fuel comparator 121 determines whether or not the flow sensed by the flow sensor 43 in this state is smaller than the target value, and if it not is smaller than the target value, then it is determined whether or not the flow is equal to the target value (S402 and S403 in FIG. 14).

If the flow is equal to the target value in S403, setting is ended (S404 in FIG. 14). That is, the above-mentioned optimal frequency, drive voltage, and duty ratio are operationally set, and these values are stored in the memory 49. In other words, the piezoelectric pump 44 is operated by the drive application voltage (amplitude) found in S3 and by the second drive frequency and drive duty ratio found in S205.

In S403, if the flow is not equal to the target value, then in S405 the duty ratio adjuster 124 of the second adjuster 122 determines whether or not the duty ratio of the drive voltage is at the lowest value during use (10%). If the duty ratio is not under the lowest value during use (10%) here, the duty ratio is reduced by 1% by the duty ratio adjuster 124, and control processing returns to S402 (S406 and S402 in FIG. 14).

In S405 if the duty ratio adjuster 124 determines that the duty ratio has gone under the lowest value, then the applied voltage adjuster 125 determines whether or not the value of the drive voltage is the lowest value (S407 in FIG. 14).

If the value of the drive voltage is not the lowest value, the applied voltage adjuster 125 reduces the drive voltage by 0.1 V, and control processing returns to S402 (S408 and S402 in FIG. 14).

If the value of the drive voltage in S407 is the lowest value, the controller 48 causes the display component 46 to give an error display (S410 in FIG. 14).

That is, error processing is performed when the duty ratio of the drive voltage is the lowest value and the value of the drive voltage is also the lowest value.

If the second fuel comparator 121 determines in S402 that the flow sensed by the flow sensor 43 is smaller than the target value, the duty ratio adjuster 124 in S411 determines whether or not the duty ratio of the drive voltage is the highest value during use (40%), and if it is not the highest value, the duty is increased by 1% (S412 in FIG. 14), and the second fuel comparator 121 determines whether or not the flow sensed by the flow sensor 43 is equal to the target value (S413 in FIG. 14).

The setting is concluded if the flow is equal to the target value (S414 in FIG. 14). That is, the above-mentioned optimal frequency (an example of the second drive frequency), optimal drive voltage, and optimal duty are operationally set, and the third setting component 123 stores these values in the memory 49 (S414 in FIG. 14). The setting range for the duty ratio during use has a margin of 10% for the upper and lower limits from the setting range of the duty ratio during learning, and is from 10 to 40%.

If the duty ratio adjuster 124 in S411 determines that the duty of the drive voltage is the highest value during use (S415 in FIG. 14), the applied voltage adjuster 125 increases the voltage applied to the piezoelectric element by 0.1 V (S415 in FIG. 14).

Next, in this state the second fuel comparator 121 determines whether or not the flow sensed by the flow sensor 43 is equal to the target value (S416 in FIG. 14).

The setting is concluded if the flow is equal to the target value (S417 in FIG. 14). That is, the above-mentioned optimal frequency (an example of the second drive frequency), optimal drive voltage, and optimal duty are operationally set, and the third setting component 123 stores these values in the memory 49 (S417 in FIG. 14).

In S416, if the flow is different from the target value, it is then determined whether or not the flow is smaller than the target value (S418 in FIG. 14), and if it is smaller, the control processing returns to S415.

Also, in S418, if the flow is not smaller than the target value, the applied voltage adjuster 125 reduces the duty of the drive voltage by 1% (S419 in FIG. 14), and the second fuel comparator 121 again determines whether or not the flow is at the target value (S420 in FIG. 14).

In S420, if the flow is not equal to the target value, the control processing returns to S419. If the flow in S420 is equal to the target value, the setting is concluded (S421 in FIG. 14). That is, the above-mentioned optimal frequency (an example of the second drive frequency), optimal drive voltage, and optimal duty are operationally set, and the third setting component 123 stores these values in the memory 49 (S421 in FIG. 14).

The length of time over which the above operational setting of the piezoelectric pump 44 is performed (S205 in FIG. 12) is 10 seconds, for example, and the time it actually takes the piezoelectric pump 44 to supply all of the exhalation in the chamber 23 to the measurement component 45 is 30 seconds. Therefore, the operational setting of the piezoelectric pump 44 (an example of the second learning control step) is concluded in the first 10 seconds of these 30 seconds. The nitrogen monoxide concentration is measured from the exhalation supplied to the measurement component 45 during the few seconds after this operational setting (S206 in FIG. 12).

Once this measurement of the exhalation is complete, the measurement controller 130 uses the drive valve 36 to close the valve hole 35 of the input gas switching device 31, and the valve hole 38 is opened up (S207 in FIG. 12).

In this state, the piezoelectric pump 44 draws in air through the one-way valve 41 of the zero gas generator 37, the valve hole 38, and the filter 42 that removes the nitrogen monoxide, and the nitrogen monoxide concentration in this air is measured by the measurement component 45 (S208 in FIG. 12).

Then, the final exhalation concentration is calculated from the nitrogen monoxide concentration in the exhalation measured in S206 and the nitrogen monoxide concentration in the air measured in S208 (S209 in FIG. 12). The controller 48 causes the display component 46 to display this calculation result, and then concludes the measurement (S210 and S211 in FIG. 12). The nitrogen monoxide concentration in the air measured in S208 is the value sensed by the measurement component 45 when measuring air from which nitrogen monoxide had been removed, and can also be called a blank value.

As shown in FIG. 5, the chamber 23 is provided with the intake/discharge holes 33 and 34 on the upstream and downstream sides of the outlet 32 to the input gas switching device 31 in the undulating path 30, so when exhalation is blown in, there is less resistance as it flows into the chamber 23. Also, the exhalation inside the chamber 23 can be supplied by the piezoelectric pump 44 to the measurement component 45 with less resistance.

3. Main Features 3-1

The exhalation measurement device in this implementation comprises the chamber 23, the measurement component 45, the piezoelectric pump 44, the first learning controller 100, and the second learning controller 110. The chamber 23 temporarily holds exhalation. The measurement component 45 measures a specific component in the exhalation. The piezoelectric pump 44 supplies the measurement component 45 with the exhalation held in the chamber 23. The first learning controller 100 performs operational setting of the piezoelectric pump 44 before the piezoelectric pump 44 supplies the measurement component 45 with the exhalation in the chamber 23. The second learning controller 110 performs operational setting of the piezoelectric pump 44 after the piezoelectric pump 44 has started to supply the exhalation in the chamber 23 to the measurement component 45, but before measurement is performed by the measurement component 45.

With the exhalation measurement device in this implementation, the piezoelectric pump 44 supplies the exhalation held in the chamber 23 to the measurement component 45. Since the piezoelectric pump 44 has a short stroke, there is little vibration of the exhalation supplied by the piezoelectric pump 44 to the measurement component 45, and as a result the variance in sensed values can be reduced at the measurement component 45. This allows sensing accuracy to be improved.

Also, since the optimal settings (such as drive frequency) will vary with the usage environment (such as temperature), in this implementation the operational setting of the piezoelectric pump 44 is performed before the exhalation in the chamber 23 is supplied to the measurement component 45, but after the piezoelectric pump 44 has started supplying the exhalation in the chamber 23 to the measurement component 45. Consequently, the piezoelectric pump 44 is driven in the optimal state, and as a result, the flow of exhalation supplied to the measurement component 45 is more stable, which allows sensing accuracy to be improved.

3-2

With the exhalation measurement device in this implementation, the first learning controller 100 selects the first drive frequency for driving the piezoelectric pump 44 as shown in FIGS. 9 and 11. Consequently, the drive frequency for driving the piezoelectric pump 44 can be selected.

3-3

With the exhalation measurement device in this implementation, as shown in FIGS. 9 and 13, the second learning controller 110 selects the second drive frequency from a specific region that includes ±256 Hz of the first drive frequency (an example of a specific region that includes a first drive frequency) selected in the first operational setting. Consequently, the drive frequency can be set accurately with respect to changes in the surrounding environment and so forth that occur as time passes after the first drive frequency is selected by the first learning controller 100.

3-4

As shown in FIGS. 9 and 14, the exhalation measurement device in this implementation further comprises the voltage duty ratio adjuster 120. The voltage duty ratio adjuster 120 performs duty control so that the flow will be constant, using the second drive frequency selected by the second learning controller 110. Consequently, even after the second drive frequency has been set, if the flow produced by the piezoelectric pump 44 should fluctuate due to turbulence caused by a change in the surrounding air flow, for example, control can be performed so as to keep the flow constant.

3-5

With the exhalation measurement device in this implementation, as shown in FIGS. 9 and 11, the first learning controller 100 selects the first drive frequency and selects the drive application voltage applied to the piezoelectric pump 44. Consequently, the drive application voltage and the drive frequency for driving the piezoelectric pump 44 can be selected.

3-6

With the exhalation measurement device in this implementation, as shown in FIGS. 9 and 11, the first learning controller 100 has the resonance frequency detector 101 that detects the frequency at which the piezoelectric element of the piezoelectric pump 44 resonates, by varying the frequency in a state in which 6 V (an example of a specific voltage) has been applied. The first drive frequency is the frequency of resonance. The first drive frequency for driving the piezoelectric pump 44 can be selected by thus using a frequency search to detect the frequency at which the piezoelectric element of the piezoelectric pump 44 resonates.

3-7

As shown in FIG. 3, the exhalation measurement device in this implementation comprises the zero gas generator 37 (an example of a zero gas generator), the input gas switching device 31 (an example of a switching component), and the flow sensor 43 (an example of a flow sensor). The zero gas generator 37 generates zero gas, in which nitrogen monoxide (an example of a specific component) has been removed from the air. The input gas switching device 31 switches the gas that is sent to the piezoelectric pump 44 between the exhalation inside the chamber 23 and zero gas produced by the zero gas generator 37. The flow sensor 43 measures the flow of gas pumped by the piezoelectric pump 44. As shown in FIG. 9, the first learning controller 100 has the first flow comparator 102 and the first adjuster 103. The first flow comparator 102 uses a specific applied voltage and a selected frequency to compare the flow sensed by the flow sensor 43 when the piezoelectric pump 44 was operated, and 3 mL/second (an example of a first target flow), in a state in which the gas sent to the piezoelectric pump 44 has been switched by the input gas switching device 31 to zero gas. The first adjuster 103 adjusts a specific applied voltage so that the flow sensed by the flow sensor 43 will be 3 mL/second (an example of first target flow), on the basis of the comparison performed by the first flow comparator 102. The drive application voltage is the applied voltage adjusted by the first adjuster 103.

The drive application voltage for driving the piezoelectric pump 44 can thus be found by using the first drive frequency to adjust the amount of applied voltage so that the target flow will be achieved upon driving the piezoelectric pump 44.

3-8

With the exhalation measurement device in this implementation, as shown in FIGS. 9 and 13, the second learning controller 110 selects a second drive frequency from ±256 Hz of the first drive frequency (an example of within a specific region that includes the first drive frequency), and selects a drive duty ratio that is the duty ratio of the drive application voltage. Consequently, the drive frequency for driving the piezoelectric pump 44, and the duty ratio of the drive application voltage can be selected.

3-9

The exhalation measurement device in this implementation further comprises the flow sensor 43, which senses the flow of gas pumped by the operation of the piezoelectric pump 44. As shown in FIG. 9, the second learning controller 110 has the frequency change component 111, the duty ratio increase/decrease determination component 112, and the duty ratio selector 113. The frequency change component 111 changes the first drive frequency at 20 Hz (an example of a specific frequency interval) while changing the duty ratio of the drive application voltage to keep the flow at 2 mL/second (an example of a second target flow). The duty ratio increase/decrease determination component 112 determines an increase or decrease in the duty ratio when the frequency is changed by the frequency change component 111. The duty ratio selector 113 selects the smallest duty ratio on the basis of the determined increase or decrease in the duty ratio. The second drive frequency is the frequency at which the duty ratio is the lowest. The drive duty ratio is the lowest duty ratio selected by the duty ratio selector 113. Consequently, the drive frequency for driving the piezoelectric pump 44, and the duty ratio of the drive application voltage can be selected.

3-10

The exhalation measurement device in this implementation further comprises the flow sensor 43 and the voltage duty ratio adjuster 120. The flow sensor 43 senses the flow of gas that is pumped by the operation of the piezoelectric pump 44. The voltage duty ratio adjuster 120 adjusts the drive duty ratio and the drive application voltage in a state in which the second drive frequency is fixed, so that the flow will 2 mL/second (an example of second target flow) when the piezoelectric pump 44 is operated using the second drive frequency, the drive application voltage, and the drive duty ratio, and the flow sensed by the flow sensor 43 is different from 2 mL/second. Consequently, even after the second drive frequency has been set, if the flow produced by the piezoelectric pump 44 should fluctuate due to turbulence caused by a change in the surrounding air flow, for example, the drive duty ratio and the drive application voltage can be adjusted so as to keep the flow constant.

3-11

The exhalation measurement device in this implementation comprises the zero gas generator 37 (an example of a zero gas generator) and the measurement controller 130. The zero gas generator 37 generates zero gas, in which nitrogen monoxide (an example of a specific component) has been removed from the air. The measurement controller 130 calculates the concentration of nitrogen monoxide (an example of a specific component) from the zero gas measured value measured by the measurement component 45 and the measured value for exhalation inside the chamber 23 measured by the measurement component 45.

The zero gas generator 37 has the filter 42, the opening 370a (an example of an inflow component), and the one-way valve 41. The filter 42 removes nitrogen monoxide (an example of a specific component). The opening 370a allows outside air to flow into the filter 42. The one-way valve 41 is disposed in the opening 370a and opens up when air flows into the filter 42. A slit 411 is formed in the one-way valve 41, and the filter 42 communicates with the outside via the slit 411 when the one-way valve 41 is both open and closed.

Since the slit 411 is thus formed, initial resistance can be lowered in the supply of NO zero gas to the measurement component 45 by the operation of the piezoelectric pump 44. Specifically, if the slit 411 is not formed in the one-way valve 41, initial resistance increases in order to open up the one-way valve 41, but in this implementation initial resistance can be reduced by the slit 411.

The width of the slit 411 is set so as to allow the NO removal performed by the filter 42 to be maintained for a specific length of time (such as a period established by the device specifications), and to allow a low initial resistance to be obtained. That is, since the filter 42 is always in contact with the outside air via the slit 411, it is gradually degraded, but the rate of this degradation can be reduced by narrowing the slit 411. Also, widening the slit 411 allows initial resistance to be reduced during operation of the piezoelectric pump 44, so the width dl of the slit 411 (see FIG. 7C) is set so as to strike a good balance between the rate of degradation and the initial resistance.

3-12

In this implementation, an example of the first target flow (3 mL/second) is set to be greater than an example of the second target flow (2 mL/second), as discussed above.

The sensing of the first drive frequency in FIG. 11 (an example of a first operational setting mode) only involves sensing the peak, so it is preferable for the amount of change per unit of frequency to be larger. On the other hand, the sensing of the second drive frequency in FIG. 13 is performed using the exhalation in the chamber 23 prior to measurement, so the flow during measurement is required, and a smaller flow is preferable so long as the sensor of the measurement component 45 is able to react.

Accordingly, in this implementation an example of the first target flow is set to be greater than an example of the second target flow.

3-13

The method for controlling an exhalation measurement device in this implementation is a method for controlling an exhalation measurement device that comprises the chamber 23 that temporarily holds exhalation, the measurement component 45 that measures a specific component in the exhalation, and the piezoelectric pump 44 that supplies the measurement component 45 with the exhalation held in the chamber 23, said method comprising a step S3 (an example of a first learning control step) and a step S205 (an example of a second learning control step). In S3 (the first learning control step), the operational setting of the piezoelectric pump 44 is performed before the piezoelectric pump 44 supplies the exhalation in the chamber 23 to the measurement component 45. In S205 (an example of a second learning control step), the operational setting of the piezoelectric pump 44 is performed after the piezoelectric pump 44 has started to supply the exhalation in the chamber 23 to the measurement component 45, but before measurement is performed by the measurement component 45.

With the method for controlling an exhalation measurement device in this implementation, vibration of the exhalation supplied to the measurement component 45 is reduced by using the piezoelectric pump 44. As a result, variance in the sensed value at the measurement component 45 can be reduced, and sensing accuracy can be improved.

4. Other Implementations

A

In the above implementation, the value for the first target flow in FIG. 11 is set to 3 mL/second, the second target flow in FIGS. 13 and 14 is set to 2 mL/second, and the first target flow is set to be greater than the second target flow, but the first target flow may instead be the same as the second target flow, and set to 2 mL/second.

B

As shown in FIG. 9, in the above implementation the first setting component 104 stored the first drive frequency and the drive application voltage in the memory 49, but the first setting component 104 need not be provided. In this case, the resonance frequency detected by the resonance frequency detector 101 may be sent directly to the second learning controller 110, and the applied voltage adjusted by the first adjuster 103 may be sent directly to the second learning controller 110 and the voltage duty ratio adjuster 120. Similarly, the second setting component 105 need not be provided, and the second drive frequency and the drive duty ratio may be sent directly to the voltage duty ratio adjuster 120.

INDUSTRIAL APPLICABILITY

The exhalation measurement device and method for controlling the same may have the effect of allowing sensing accuracy to be improved, and may be expected to find use in exhalation measurement devices that are used in checking pulmonary function, diagnosing asthma, and so forth.

The invention claimed is:

1. An exhalation measurement device, comprising:
a chamber that temporarily holds exhalation;
a measurement component that measures a specific component in the exhalation;
a piezoelectric pump that supplies the measurement component with the exhalation held in the chamber;
a first learning controller that performs a first operational setting on the piezoelectric pump before the piezoelectric pump supplies the exhalation in the chamber to the measurement component;
a second learning controller that performs a second operational setting on the piezoelectric pump after the piezoelectric pump has started supplying the exhalation in the chamber to the measurement component, but before the measurement component performs its measurement, and
a flow sensor that senses a flow of gas supplied by the operation of the piezoelectric pump,
wherein the first learning controller selects a first drive frequency for driving the piezoelectric pump, and
wherein the second learning controller selects a second drive frequency from within a specific range that includes the first drive frequency selected by the first learning controller, and selects a drive duty ratio that is a duty ratio of a drive application voltage;
the second learning controller has:
a frequency change component that changes the first drive frequency at a specific frequency interval while changing the duty ratio of the drive application voltage to maintain the flow of gas at a second target flow;
a duty ratio increase/decrease determination component that determines an increase or decrease in the duty ratio when the frequency is changed by the frequency change component; and
a duty ratio selector that selects a smallest duty ratio representing a minimum within a range of the determined increase or decrease in the duty ratio when the frequency has been changed,
the second drive frequency is the frequency at the smallest duty ratio, and
the drive duty ratio is the smallest duty ratio selected by the duty ratio selector; and
a voltage duty ratio adjuster that uses the second drive frequency selected by the second learning controller to control the duty ratio of the drive application voltage that is applied to the piezoelectric pump so that a flow rate is constant.

2. The exhalation measurement device according to claim 1,
wherein the first learning controller also selects the drive application voltage that is applied to the piezoelectric pump.

3. The exhalation measurement device according to claim 2,
wherein the first learning controller has a resonance frequency detector that detects the first drive frequency at which a piezoelectric element of the piezoelectric pump resonates by varying the first drive frequency in a state in which a specific drive application voltage has been applied, and
the first drive frequency is a frequency of resonance.

4. The exhalation measurement device according to claim 2, comprising:
a zero gas generator that generates zero gas, the zero gas being obtained by eliminating the specific component from air;
a switching component that switches a gas sent to the piezoelectric pump between the exhalation inside the chamber and the zero gas generated by the zero gas generator; and
wherein the first learning controller has:
a first flow comparator that compares a first target flow to the flow of gas sensed by the flow sensor when the piezoelectric pump is operated using a specific application voltage and the first drive frequency in a state in which the gas sent to the piezoelectric pump has been switched by the switching component to zero gas; and
a first adjuster that adjusts the specific application voltage so that the flow of gas sensed by the flow sensor on the basis of the comparison performed by the first flow comparator will become the first target flow, and
the drive application voltage is the specific application voltage adjusted by the first adjuster.

5. The exhalation measurement device according to claim 4,
wherein
the first target flow is set to be larger than the second target flow.

6. The exhalation measurement device according to claim 1,
wherein the voltage duty ratio adjuster is configured to adjust the drive application voltage and the drive duty ratio in a state in which the second drive frequency is fixed, so that the flow of gas will become the second target flow when the piezoelectric pump is operated using the second drive frequency, the drive application voltage, and the drive duty ratio; and
the drive duty, and the second target flow is different from the flow of gas sensed by the flow sensor.

7. The exhalation measurement device according to claim 1, further comprising:
a zero gas generator that generates a zero gas, which is obtained by eliminating the specific component from air; and
a measurement controller that calculates a concentration of the specific component from a measured value for the exhalation in the chamber measured by the measurement component, and a measured value for the zero gas measured by the measurement component,
wherein the zero gas generator has:
a filter that eliminates the specific component;
an inflow component where gas flows into the filter; and
a one-way valve that is disposed in the inflow component, and is in its open state when the gas flows into the filter, a slit is formed in the one-way valve, and
the filter communicates with the outside through the slit in both the open state and a closed state of the one-way valve.

8. A method for controlling an exhalation measurement device comprising a chamber that temporarily holds exhalation, a measurement component that measures a specific component in the exhalation, and a piezoelectric pump that supplies the measurement component with the exhalation held in the chamber, said method comprising:
   a first learning control step of performing a first operational setting of the piezoelectric pump before the piezoelectric pump supplies the exhalation in the chamber to the measurement component;
   a second learning control step of performing a second operational setting of the piezoelectric pump after the piezoelectric pump has started supplying the exhalation in the chamber to the measurement component, but before the measurement component performs its measurement,
   wherein the first learning control step involves selecting a first drive frequency for driving the piezoelectric pump, and
   wherein the second learning control step involves selecting a second drive frequency from within a specific range that includes the first drive frequency selected in the first learning control step, and selecting a drive duty ratio that is a duty ratio of a drive application voltage;
   the second learning control step involves a frequency change operation in which the first drive frequency is changed at a specific frequency interval while the duty ratio of the drive application voltage is changed to maintain a flow of gas at a second target flow;
   a duty ratio increase/decrease determination operation that determines an increase or decrease in the duty ratio when the frequency is changed in the frequency change operation; and
   a duty ratio selection operation in which a smallest duty ratio is selected on the basis of the determined increase or decrease in the duty ratio, the second drive frequency is a frequency at which the duty ratio is the smallest duty ratio, and
   the drive duty ratio is the smallest duty ratio selected by the duty ratio selector; and
   a voltage duty ratio adjustment step of using the second drive frequency selected in the second learning control step to control the duty ratio of the drive application voltage that is applied to the piezoelectric pump so that a flow rate will be constant.

9. The method for controlling an exhalation measurement device according to claim 8,
   wherein the first learning control step involves selecting the drive application voltage that is applied to the piezoelectric pump.

10. The method for controlling an exhalation measurement device according to claim 9,
    wherein the first learning control step involves a resonance frequency detecting operation in which the first drive frequency at which a piezoelectric element of the piezoelectric pump resonates is detected by varying the first drive frequency in a state in which a specific voltage has been applied, and
    the first drive frequency is a frequency of resonance.

11. The method for controlling an exhalation measurement device according to claim 9,
    wherein the first learning control step involves:
    a first flow comparison operation in which a first target flow is compared to a flow of gas when the piezoelectric pump is operated using a specific application voltage and the first drive frequency in a state in which zero gas, from which the specific component has been removed from the air, is being sent to the piezoelectric pump; and
    a first adjustment operation in which the specific application voltage is adjusted so that the flow of gas moved by the piezoelectric pump will be the first target flow, on the basis of the comparison performed in the first flow comparison operation, and
    the drive application voltage is the application voltage adjusted in the first adjustment operation.

12. The method for controlling an exhalation measurement device according to claim 11,
    wherein
    the first target flow is set to be larger than the second target flow.

13. The method for controlling an exhalation measurement device according to claim 8,
    wherein the voltage duty ratio adjustment step adjusts the drive application voltage and the drive duty ratio in a state in which the second drive frequency is fixed, so that a flow of gas will become the second target flow when the second target flow is different from the flow when the piezoelectric pump is operated using the second drive frequency, the drive application voltage, and the drive duty ratio.

* * * * *